(12) United States Patent
Nelson et al.

(10) Patent No.: US 6,887,713 B2
(45) Date of Patent: May 3, 2005

(54) BIOACTIVE CHIP MASS SPECTROMETRY

(75) Inventors: Randall W. Nelson, Phoenix, AZ (US); Dobrin Nedelkov, Tempe, AZ (US)

(73) Assignee: Intrinsic Bioprobes, Inc., Tempe, AZ (US)

( * ) Notice: Subject to any disclaimer, the term of this patent is extended or adjusted under 35 U.S.C. 154(b) by 0 days.

(21) Appl. No.: 10/357,981

(22) Filed: Feb. 4, 2003

(65) Prior Publication Data

US 2004/0126894 A1 Jul. 1, 2004

Related U.S. Application Data

(63) Continuation of application No. 09/523,762, filed on Mar. 11, 2000, now Pat. No. 6,569,383.

(51) Int. Cl.[7] .......................... G01N 24/00; G01N 1/00; G01N 1/18; G01N 21/00; G01N 15/06
(52) U.S. Cl. ........................ 436/173; 436/174; 436/175; 436/177; 436/63; 436/501; 436/518; 422/50; 422/55; 422/58; 422/68.1; 435/6; 435/7.1
(58) Field of Search ........................... 422/50, 68.1, 83, 422/61, 58, 57; 436/501, 518, 173, 63; 435/6, 23, 7.1, 24

(56) References Cited

U.S. PATENT DOCUMENTS

| | | | |
|---|---|---|---|
| 5,304,487 A | | 4/1994 | Wilding et al. |
| 5,632,957 A | | 5/1997 | Heller et al. |
| 5,770,272 A | * | 6/1998 | Biemann et al. ............ 427/421 |
| 5,856,082 A | | 1/1999 | Aebersold et al. |
| 5,872,010 A | | 2/1999 | Karger et al. |
| 5,955,729 A | | 9/1999 | Nelson et al. |
| 6,004,770 A | | 12/1999 | Nelson |
| 6,225,047 B1 | | 5/2001 | Hutchens et al. |
| 6,274,089 B1 | | 8/2001 | Chow et al. |
| 6,322,970 B1 | | 11/2001 | Little et al. |

OTHER PUBLICATIONS

WO 94/28418 (PCT//US94/06064) (Hutchens et al).*
Karas, M., U. Bahr, A. Ingendoh, E. Nordhoff, B. Stahl, K. Strupat and F. Hillenkamp, Principles and application of matrix–assisted U– laser desorption/ionization mass spectrometry, Analytica Chimica Acta, 241 (1990) 175–185, Elsevier Science Publishers B. V., Amsterdam.
Amankwa, Lawrence N. and Werner G. Kuhr, Trypsin–Modified Fused–Silica Capillary Microreactor for Peptide Mapping by Capillary Zone Electrophoresis, Anal. Chem. 1992, 64, 1610–1613.

* cited by examiner

Primary Examiner—Jill Warden
Assistant Examiner—Brian Sines
(74) Attorney, Agent, or Firm—Snell & Wilmer L.L.P.

(57) ABSTRACT

The present invention is directed to a bioactive probe or chip (BC) that allows for the isolation of analytes, such as biomolecules, followed by modification or bioreaction on these said analytes. More specifically, the present invention relates to various methods and apparatuses that include the BC and further include characterization and identification technologies, such as Bioactive Chip Mass Spectrometry (BCMS). Within the context of the present invention, BC provides a method and device for the capture and subsequent modifying, such as digestion or derivatization, of an analyte. Further, real-time information regarding a variety of molecular interactions may be provided by techniques such as interaction analysis (IA). Finally, the variety of molecules are localized and concentrated thereby aiding in the identification and/or quantification of the molecules by techniques such as mass spectroscopy. In one embodiment, a method for performing the modification, or bioreaction, of biomolecules is disclosed. Preferably, the method involves capturing an analyte present within a sample by an interactive surface layer located in a separation site; washing unwanted portions of the sample from the surroundings of the captured analyte; transferring the captured analyte from the separation site to a modifying site; modifying or bioreacting the analyte to create a modified or bioreacted analyte. The modified analyte may then be subsequently characterized and/or identified by techniques such as mass spectrometry.

10 Claims, 11 Drawing Sheets

FIG. 6a
FIG. 6b
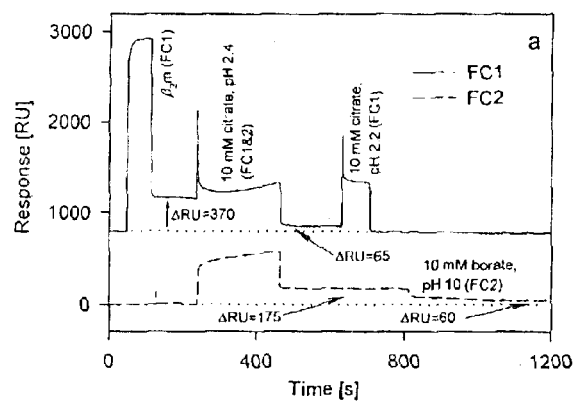
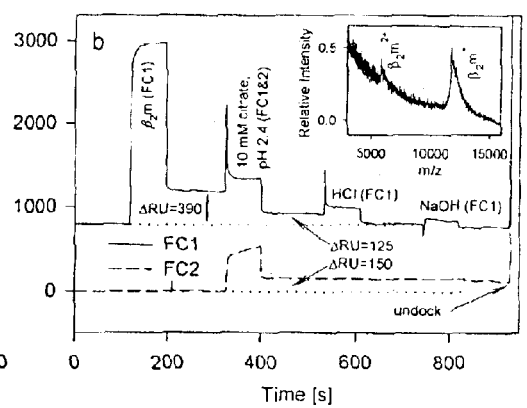

SEQUENCE LISTING

<160> NUMBER OF SEQ ID NOS: 5

<210> SEQ ID NO 1
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Gly Thr Ser Phe His Pro Gln Trp Ile Met Val Gly Lys Val Ala
  1               5                  10                  15

Thr Asn Ser Pro
            20

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Gly Thr Ser Phe His Pro Gln Trp Ile Met Val Gly Arg Val Ala
  1               5                  10                  15

Thr Asn Ser Pro
            20

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Glu Lys His His Ser His
  1               5

<210> SEQ ID NO 4
<211> LENGTH: 126
<212> TYPE: PRT
<213> ORGANISM: Homo sapiens
<220> FEATURE:
<221> NAME/KEY: MOD_RES
<222> LOCATION: (30)
<223> OTHER INFORMATION: Val or Met

<400> SEQUENCE: 4

Gly Pro Thr Gly Thr Gly Glu Ser Lys Cys Pro Leu Met Val Lys Val
  1               5                  10                  15

Leu Asp Ala Val Arg Gly Ser Pro Ala Ile Asn Val Ala Xaa His Val
                 20                  25                  30

Phe Arg Lys Ala Asp Asp Thr Trp Glu Pro Phe Ala Ser Gly Lys Thr
             35                  40                  45

Ser Glu Ser Gly Glu Leu His Gly Leu Thr Thr Glu Glu Phe Val
         50                  55                  60

Glu Gly Ile Tyr Lys Val Glu Ile Asp Thr Lys Ser Tyr Trp Lys Ala
 65                  70                  75                  80

-continued

```
Leu Gly Ile Ser Pro Phe His Glu His Ala Glu Val Val Phe Thr Ala
                85                  90                  95

Asn Asp Ser Gly Pro Arg Arg Tyr Thr Ile Ala Ala Leu Leu Ser Pro
            100                 105                 110

Tyr Ser Tyr Ser Thr Thr Ala Val Val Thr Asn Pro Lys Glu
        115                 120                 125

<210> SEQ ID NO 5
<211> LENGTH: 71
<212> TYPE: PRT
<213> ORGANISM: Artificial Sequence
<220> FEATURE:
<223> OTHER INFORMATION: Description of Artificial Sequence: Synthetic
      illustrative peptide
<220> FEATURE:
<221> NAME/KEY: MOD_RES
<222> LOCATION: (61)
<223> OTHER INFORMATION: Asn or Asp
<220> FEATURE:
<221> NAME/KEY: MOD_RES
<222> LOCATION: (63)
<223> OTHER INFORMATION: Asn or Asp

<400> SEQUENCE: 5

Ile Arg Cys Phe Ile Thr Pro Asp Ile Thr Ser Lys Asp Cys Pro Asn
  1               5                  10                  15

Gly His Val Cys Tyr Thr Lys Thr Trp Cys Asp Ala Phe Cys Ser Ile
             20                  25                  30

Arg Gly Lys Arg Val Asp Leu Gly Cys Ala Ala Thr Cys Pro Thr Val
         35                  40                  45

Lys Thr Gly Val Asp Ile Gln Cys Cys Ser Thr Asp Xaa Cys Xaa Pro
     50                  55                  60

Phe Pro Thr Arg Lys Arg Pro
 65                  70
```

BIOACTIVE CHIP MASS SPECTROMETRY

REFERENCE TO RELATED APPLICATIONS

This application is a Continuation of U.S. patent application Ser. No. 09/523,762, filed Mar. 11, 2000 now U.S. Pat. No. 6,569,383, and entitled "BIOACTIVE CHIP MASS SPECTROMETRY".

GRANT SUPPORT

Financial assistance for some of the work reported herein was provided by the National Institutes of Health, under grant number 1 R43 CA82079-01. The National Institute of Health may own certain rights to this invention.

FIELD OF INVENTION

This invention is generally directed to a chip-based element for the stepwise bioselection, bioreaction, characterization, and identification of biomolecules. More specifically, the bioactive chip or probe is capable of separation of biomolecules residing in complex mixtures, post-separation processing and/or modifying, and complete structural characterization of the processed and/or modified biomolecules by mass spectrometry.

BACKGROUND OF THE INVENTION

Massive, worldwide efforts over the past few decades have resulted, or will soon result, in the complete genome sequencing of a number of select organisms. Once completed and cataloged into databases, these genomes represent virtual libraries that can be translated into all of the potential proteins contained within their respective organisms. In this regard, genome databases become a foundation for the much broader field of proteomics, wherein the structure and function of specific proteins are under investigation. Such studies are intrinsically complicated, representing multi-dimensional problems that are both qualitative and quantitative in nature. To begin with, a protein of interest will generally reside in complex biological systems and oftentimes represents only a small fraction of the total protein content of the system. The efficient fractionation of the protein from bulk endogenous compounds is therefore necessary for any further characterization.

Once isolated, the protein must be characterized in terms of structure. The focus of these analyses ranges from primary (amino acid sequence) through tertiary (three-dimensional structure due to protein folding) structure, as well as post-translational modifications. Proteome investigation then takes on the new dimension of protein function, with emphasis placed on quaternary structure (polypeptide complexes resulting in functional proteins) and the determination of biomolecular interaction partners (receptor-ligand interactions).

Finally, it is often necessary to quantitatively monitor expression profiles to better understand protein function as a part of a complete cellular system.

In all, it is accurate to say that proteome investigations demand much of analytical sciences and corresponding instrumentation. Thus, there exists a growing need for concerted, multi-analytical approach capable of high-sensitivity analyte fractionation and characterization of protein structure and function.

Multidimensional chip-integrated microarrays that encompass both selective protein fractionation and complete structural/functional characterization would satisfy the need for such proteome analysis using "lab-on-a-chip" approaches. These chip-based microarrays must be combined with a microfluidics system able to precisely deliver a sample to specialized sites on the chip that are capable of analyte fractionation and subsequent processing and/or modifications. The chip based microfluidics systems preferably includes a form of detection for sensing the isolation of an analyte and for tracking the location of the analyte on the array during manipulation. Finally, the system must be capable of providing defining structural information on the analyte, such as sequence verification and/or identification, and detection of point mutations and post-translational modification, thereby resulting in analyte identification.

In 1988, matrix-assisted laser desorption/ionization time-of-flight (MALDI-TOF) mass spectrometry (MS) was introduced by Hillenkamp and Karas (*Anal. Chem.* 60:2288–2301, 1988), and, has since become a valuable tool for protein characterization and identification. Briefly, MALDI-TOF mass spectrometry is based on the ability to generate intact vapor-phase ions of large, thermally labile biomolecules by desorption/ionization from a matrix comprised of small volatile (matrix) molecules and the biomolecules studied. Pulsed laser radiation, tuned to an absorption maximum of the matrix is used to initiate the desorption/ionization event and to simultaneously generate a packet of ions of different mass-to-charge ratio (m/z). These ions are accelerated to the same electrostatic potential and allowed to drift an equal distance before striking a detector. The mass of the ions is determined by equating the flight times of the ions to m/z.

The success of MALDI-TOF mass spectrometry in the area of protein science can be attributed to several factors. The greatest of these is that MALDI-TOF can be rapidly (~5 minutes) applied as an analytical technique to analyze small quantities of virtually any protein (practical sensitivities of ~1 pmole protein loaded into the mass spectrometer). The technique is also extremely accurate in identifying biomolecules. Beavis and Chait demonstrated that the molecular masses of peptides and proteins can be determined to within 0.01% by using methods in which internal mass calibrants (x-axis calibration) are introduced into the analysis (*Anal. Chem.* 62:1836–40, 1990).

MALDI-TOF can also be quantitatively used with a similar method in which internal reference standards are introduced into the analysis for ion signal normalization (y-axis calibration) with accuracies on the order of 10% (Nelson et al., *Anal. Chem.* 66:1408–15, 1994).

Finally, MALDI-TOF is extremely tolerant of large molar excesses of buffer salts and, more importantly, the presence of other proteins, making it a practical approach for directly analyzing complex biological mixtures. Many examples exist where MALDI-TOF is used to directly analyze the results of proteolytic or chemical degradation of polypeptides. Other examples extend to elucidating post-translational modifications (namely carbohydrate type and content), a process requiring the simultaneous analysis of components present in a heterogeneous glycoprotein mixture (Sutton et al., *Techniques in Protein Chemistry III*, Angeletti, Ed., Academic Press, Inc., New York, pp. 109–1 16, 1993). Arguably, the most impressive use of direct mixture analysis is the screening of natural biological fluids. In this application, proteins are identified, as prepared directly from the host fluid, by detection at precise and characteristic mass-to-charge (m/z) values (Tempst et al., *Mass Spectrometry in the Biological Sciences*, Burlingame and Carr, Ed., Humana Press, Totowa, N.J., p. 105, 1996).

While the above examples involving direct MALDI-TOF analysis of complex mixtures are quite impressive, there exist limits to the extent of practical application. These limits are reached when a target analyte is a minor component of the mixture, and is present at low concentration. A common occurrence in such situations is that the target analyte is never observed in the MALDI-TOF mass spectrum. This lack of detection is generally due to the low concentration of the analyte, yielding ion signals at or below the instrumental limits of detection. This effect is further exacerbated by protein-analyte interactions "stealing" analyte molecules from the MALDI-TOF process and/or a high instrumental baseline produced from other proteins present in the mixture resulting in "analyte masking". Methods for the selective concentration of specific species in the mixture were therefore required in order to achieve ion signals from the target analyte.

Biomolecular Interaction Analysis (BIA) is a technique capable of monitoring interactions, in real time and without the use of labels, between two or more molecules such as proteins, peptides, nucleic acids, carbohydrates, lipids and low molecular weight molecules (i.e. signaling substances and pharmaceuticals). Molecules do not need to be purified or even solubilized for BIA, but can be studied in crude extracts as well as anchored in lipid vesicles, viruses, bacteria and eucaryotic cells. In one form, the detection of molecular interactions in BIA is via Surface Plasmon Resonance (SPR), taking form of SPR-BIA. The detection principle of SPR-BIA relies on the optical phenomenon of SPR, which detects changes in the refractive index of the solution close to the surface of a sensor device, or chip. An SPR sensor consists of a transparent material having a metal layer deposited thereon. One of the interactants (e.g., receptor) is immobilized on the metal surface layer of the sensor that forms one wall of a micro-action site. A light source generates polarized light that is directed through a prism, or diffraction grating, striking the metal layer-transparent material interface. A detector detects light reflected from the metal surface. A sample containing the other interaction partner is injected in a controlled flow over the surface containing the bound interactant. Any change in the surface concentrations resulting from an interaction between the two, or more, interactants, is spectroscopically detected as an SPR signal by the shifting of relative reflective intensity signals. A continuous display of the SPR signal, as a function of time, yields a "sensorgram" that provides a complete record of the progress of associations and disassociations. When analysis of one interaction cycle is completed, the surface of the sensor can be regenerated by treatment with conditions that remove all bound analytes without affecting the activity of the immobilized ligand. SPR-BIA has become a valuable tool for the functional characterization of proteins and is broadly used for determining the kinetic and affinity parameters involved in biomolecular interactions; however, no structural information on the interacting biomolecules can be gained from the SPR-BIA analysis.

In a recent invention, SPR-BIA and MALDI-TOF MS were combined in a method that allows selective retrieval and retention of an analyte from solution on a sensor chip (monitored by SPR-BIA), followed by MALDI-TOF MS analysis of the sensor chip, yielding the mass of the retained analyte (see U.S. Pat. No. 5,955,729 entitled "Surface Plasmon Resonance-Mass Spectrometry (SPR-MS)". Thereby, this method performs a selective concentration of specific analytes from the analyzed mixture in quantities sufficient to achieve analyte ion signals for MALDI-TOF MS. Whereas the SPR-MS combination represents an important improvement over the SPR-BIA analysis alone and allows for functional concentration of a targeted analyte (important for MALDI-TOF MS analysis of low-level analytes), both SPR-BIA and SPR-MS have been limited to analyzing biomolecules as they exist in the solution, which, in many instances, can not provide enough information for the biomolecules identification. Frequently, in order to fully characterize and identify certain biomolecules, modification or derivatization is required.

Thus, there is a need for devices and methods that allow for the isolation of small quantities of biomolecules from a complex solution and that are able to modify, or bioreact, these biomolecules to create characteristic fragments, derivatives and the like. Accordingly, a variety of chemistries, enzymologies, characterizations and identification techniques may be employed after analyte isolation to gain information on both original and reacted biomolecules. Importantly, these chemistries, enzymologies, characterizations and identification techniques must be performed in manners that do not introduce interfering artifacts, e.g., backgrounds arising from the modifying reagents, the immobilized receptor responsible for isolating the analyte or from instrumental changes, into the analysis. Therefore, it is preferred to perform these characterizing modifications using: immobilized reagents, such as enzymes and the like (to preclude the introduction of reagent-induced artifacts), which are present at different sites than the receptor (such as not to introduce artifacts due to the receptor), and that analyses are performed on the same platform (such as to minimize instrumental changes). The present invention fulfills these needs, and provides further related advantages

SUMMARY OF THE INVENTION

Briefly stated, the present invention is directed to a bioreactive probe or chip (BC) that allows for the isolation of analytes, such as biomolecules, followed by modification or bioreaction on these said analytes. More specifically, the present invention relates to various methods and apparatuses that include the BC and further include characterization and identification technologies, such as Bioactive Chip Mass Spectrometry (BCMS).

Within the context of the present invention, BC provides a method and device for the capture and subsequent digestion or derivatization of an analyte. Further, real-time information regarding a variety of molecular interactions may be provided by techniques such as interaction analysis (IA). Finally, the variety of molecules is localized and concentrated thereby aiding in the identification and/or quantification of the molecules by techniques such as mass spectroscopy (MS).

In one embodiment, a device for performing BCMS is disclosed. Preferably, the device consists of a chip with separate addressable sites, these sites created for the purposes of analyte separation, processing and modification.

In a related embodiment, a device in which the addressable sites present on the chip are brought into fluid communication with each other is disclosed. Preferably, the chip has separate addressable sites for the purposes of analyte separation, processing and modification is used in conjunction with a microfluidics system capable of precise delivery, in terms of location, time and volume, of analyte to each of the addressable sites present on the chip.

In yet another embodiment, a device consisting of a chip with a microfluidics system used in combination with optical monitoring is disclosed. In this embodiment, the chip is comprised of separate addressable sites for the purposes of analyte separation, processing, and modification, and is used in conjunction with a microfluidics system capable of precise delivery of analyte to each of the addressable sites present on the chip, and is further used in combination with an optical monitoring, such as SPR, to track the precise location of the analyte and monitor progress throughout the analytical process.

In a further embodiment, a device for BCMS is disclosed. Preferably, a chip comprised of separate addressable sites for the purposes of analyte separation, processing and modification is used in conjunction with a microfluidics system capable of precise delivery of analyte to each of the addressable sites present on the chip. Optical monitoring, in the form of SPR, is used to track the precise location of the analyte and monitor progress throughout the analytical method, after which mass spectrometry, in the form of MALDI-TOF, is used to structurally characterize the analyte and modified analyte resulting from the analytical method.

In another embodiment, a method for performing the modification, or bioreaction, of biomolecules is disclosed. Preferably, the method involves capturing an analyte present within a sample by an interactive surface layer located in a separation site; washing unwanted portions of the sample from the surroundings of the captured analyte; transferring the captured analyte from the separation site to a modifying site; and modifying or bioreacting the analyte to create a modified or bioreacted analyte. The modified analyte may then be subsequently characterized and/or identified by techniques such as mass spectrometry.

In another embodiment, a method for performing activated bimolecular interaction analysis is disclosed. Preferably using surface plasmon resonance-mass spectroscopy on the sample. The method involves capturing an analyte present within the sample by an interactive surface layer of an IA sensor located in a separation site; washing unwanted biomolecules from the surroundings of the captured analyte; transferring the captured analyte from the separation site to a modifying site; bioreacting the analyte to create an modified or bioreacted analyte; analyzing the activated analyte by techniques such as surface plasmon resonance while the analyte is captured by an interactive surface layer of the bioactive chip BC located in either or both the separation and/or modifying sites; and, optionally, identifying the activated analyte by desorbing/ionizing the activated analyte from the interactive surface layer of the bioactive chip BC located on the modifying site while under vacuum within a mass spectrometer.

In yet another embodiment, a method for the analysis of multiple analytes present in a sample is disclosed. In this embodiment, a sample containing multiple analytes is brought in contact with an separation site present on the surface of a chip derivatized with a receptor. SPR is used to monitor the interaction between the immobilized receptor and the analytes, after which mass spectrometry, in the form of MALDI-TOF, is used to determine the number and nature of analytes retrieved by the receptor.

The novel features that are considered characteristic of the invention are set forth with particularity in the appended claims. The invention itself, however, both as to its structure and its operation together with the additional object and advantages thereof will best be understood from the following description of the preferred embodiment of the present invention when read in conjunction with the accompanying drawings. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. § 112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

BRIEF DESCRIPTION OF THE DRAWINGS

FIG. 6 illustrates the functional combination and operation of separation site SS and processing site PS on a bioactive chip BC. Shown are sensorgrams of beta-2-microglobulin ($\beta_2$m) retrieval in the separation site SS, subsequent routing and capture in the processing site PS, and elution from the processing site PS (a) or MALDI-TOF MS analysis form the processing site PS (b). The details of the operations are indicated on the figures. Cation exchange surface (carboxymethyldextran) was utilized in the processing site PS.

DETAILED DESCRIPTION OF THE INVENTION

Figure 1:
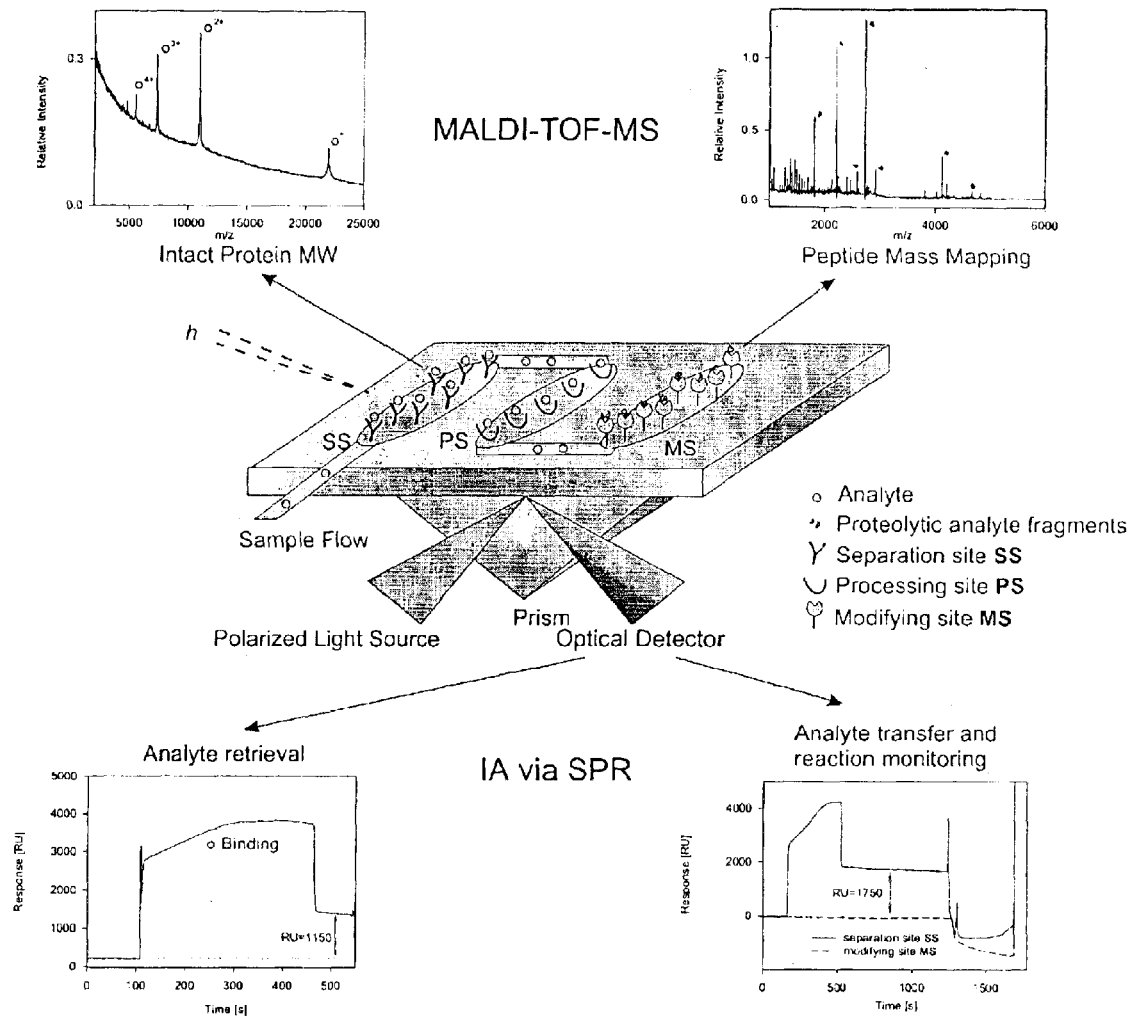
FIG. 1 is a schematic representation of a bioactive chip BC and Bioactive Chip Mass Spectrometry BCMS.

The present invention is a Bioactive Chip or probe (BC). By design, the bioactive chip BC is an arrayed, chip-based platform meant for use in the rigorous investigation of trace-level molecules, such as proteins, present in complex biological mixtures. The BC is particularly useful for the separation, processing, and modification of analytes, such as biomolecules, isolated from complex solutions. Additionally, the BC is useful for the identification of these isolated analytes by creating derivatives of the analytes that provide additional and crucial structural information on the original analyte. Furthermore, the BC can be coupled with interaction analysis (IA) and mass spectrometry (MS) to make a Bioactive Chip Mass Spectrometry (BCMS) platform. The bioactive chip BC and BCMS signify the first "lab-on-a-chip" approach capable of molecular separation, processing and structural analysis of analytes present in at low levels in complex solutions. BC, and more specifically BCMS, offers an extremely rapid, sensitive and accurate means of characterizing biological systems. In testing (Examples 1-9) BCMS demonstrates femtomole sensitivities, requires less than three hours, and generally demonstrates high-accuracy quantitative estimates and mass determination. These characteristics translate to the ability to perform several iterations of an experiment in a very short amount of time.

The need for such a concerted analytical approach is emphasized by the fact that BCMS represents one of only a few multiplexed chip-based biomolecular characterization techniques capable of the detection, unambiguous identification and quantitation of proteins retrieved from complex biological mixtures. The present invention provides methods and devices that enable a concerted analysis capable of monitoring biomolecular recognition events, and structurally characterizing the interacting partners. By multiplexing analytical techniques, BCMS is capable of bi-modal detection of target biomolecules with high specificity and sensitivity. The dual detection is also capable of quantifying the amount of target analyte present in a complex mixture, (e.g., via SPR-BIA), and then differentiating specific modifications or mutations of the target (e.g., via MS). Additionally, the component techniques of BCMS are traditionally used for different analytical purpose: SPR-BIA in function-related studies, MS used to investigate structure. Thus, the combined analysis is capable of providing complementary data, leading to a more comprehensive analysis of interacting species.

SPR-BIA and MALDI-TOF are individually capable of analyzing multiple components involved in complexes. For instance, multi-component complexes can be built on the surface of the bioactive chip BC, with each component contributing to the SPR response. When applied to complex mixtures, the combined analysis is capable of rapidly screening for, and potentially identifying, unknown interactants, or can be used to determine stoichiometries of binding or the presence of co-factors/effectors. When considering a BCMS analysis, the BIA portion of the operation performs the dual function of analyzing an interaction non-destructively, and localizing the analyte to a very defined area on the surface of the bioactive chip BC. In this regard, BIA serves both as an analysis, and as a preparation step for subsequent analyte modification and identification using MALDI-TOF MS.

A further preferred benefit of the analysis is the determination of the amount of biomolecules immobilized to the action sites via IA, preferably SPR. Such knowledge is of great value when evaluating the activity of enzyme versus immobilization chemistry, or for gauging the amount of time necessary for proteolysis of the analyte. Moreover, because the SPR response is related to a refractive index change, the exact whereabouts of solvent fronts (e.g., between buffers and eluents differing in refractive index) on the surface of the bioactive chip BC is known—allowing trace amounts of sample to be tracked throughout the BCMS process. By employing the non-destructive monitoring techniques provided by IA with SPR detection, the affinity interaction is left with the binding partners intact and recoverable for further analysis. Thus, the present invention avoids the destruction of sample via mass spectrometry without first taking advantage of non-destructive affinity interaction assay techniques. Furthermore, real-time non-destructive monitoring can be used to evaluate the initial modification or derivatization of the bioactive surface (the process of covalently binding the receptor) to ensure the viability of the affinity reagent by determining the quantity of receptor bound to the surface.

FIG. 1 conceptually illustrate the basis of BC, and BCMS, respectively. Different areas of the bioactive chip BC (action sites such as separation sites SS, processing sites PS, and modifying sites MS) are responsible for different operations on the analyte. Microfluidics are used to manipulate analyte movement across the surface of the bioactive chip BC. The bioactive chip BC allows small volumes (~50 nL) of solution and low levels of analyte (femtomole amounts) to be manipulated. Additionally, the bioactive probes may be thermally controlled and modification reactions can be performed over a range of temperatures (typically 10–40° C.).

Although bioactive chip BC technology is simple in concept, in practice it is not. Simply put, the surface chemistries typically used in different processing steps and for different analytical techniques are not necessarily compatible. For example, SPR-BIA conditions are not ideal for MS, and vice versa. Further, elution conditions from a separation site SS (e.g., low pH) will generally not be ideal for subsequent bioreactive enzymologies in a modifying site MS. Surface chemistries and accompanying analytical protocols should maintain the optimal functionality of the component techniques, as well as the combined analysis. The success of the present invention is the ability to design combinations of capture, exchange, and enzymatic reactions that can be used for different protein characterization. The overall sensitivity of BCMS is governed by two factors, the intrinsic sensitivity of the root analytical techniques and experimental design. Both SPR-based interaction analysis and MALDI-TOF mass spectrometry are equally sensitive when used individually and equally sensitive in a concerted analysis, if appropriate sample preparation methods are used.

First and foremost, the bioactive chip BC must capable of efficient and selective fractionation of analytes while maintaining high sensitivity. Because most proteins of interest reside naturally in a complex biological mixture, fractionation (or separation) of the protein from bulk endogenous compounds is a prerequisite to any further characterization. The device and method, according to the present invention, provide for fractionation that is accomplished through an immobilized receptor, such as an affixed molecule, located on separation site SS on the bioactive chip BC. In cases where the receptor's function is known (e.g., antibodies), SPR provides a relative quantitative read on the amount of analyte retained from, and/or present in, a solution. MALDI-TOF MS, as a second and more specific form of detection, is able to verify that retained analytes are in fact those thought to be retained by the receptor—registering at correct molecular masses. Mass selective detection also provides the ability to construct multi-analyte assays on the bioactive chip BC in which multiple receptors are immobilized, individually or in pairs, on separated active sites present on the bioactive chip BC. Using these assays, it is possible to screen biofluids for clinically-related biomarkers in a single analysis.

When using BCMS in the discovery mode, an element of an interaction pathway/system would be used as an affinity "hook" to retrieve interacting partners from biological fluid. In known systems, interactions could be monitored, using SPR, as a function of mutation within the "hook" to determine what effect the mutation has on the affinity of the interaction. During such analyses, and especially in cases of multiple interacting partners (complexes), MS would be used differentially to determine whether the mutation increased or reduced the number of components involved in the complex (relative to the wild-type). In cases of unknown systems, the "hook" would be used to retrieve interacting partners from solution (as recognized via SPR-detection) and MS used to catalog (number and molecular mass) and potentially identify (with enzyme processing and MS/MS) the interacting species.

Altogether, BCMS is extremely useful in the "ligand fishing" of target analytes from a natural biological carrier, the recognition of non-targeted compounds retained on the bioactive chip BC, and the analysis of multi-component binding systems. The BCMS analysis can be further enhanced by performing MALDI-TOF MS quantitatively, to determine the relative contribution of multiple binding partners to an interaction analysis curve.

Once the analyte is captured, it is important to maintain control of the small amounts (and volumes) of analyte throughout subsequent transfers and operations. It is therefore necessary to employ an efficient low-volume microfluidics system capable of transferring sub-microliter volumes of solution to different sites on the chip-based array with great precision, and to view the transfers with e.g., SPR. The system must also make provisions for exchanging buffers between elution (of an analyte from an immobilized receptor on the separation site SS) and subsequent, post-capture modification, or processing, of the analyte in the processing site PS. The processing sites PS, or exchange surfaces, should be general in nature (thus allowing the application to a wide range of analytes), be able to re-capture the analyte (with high efficiency while in the presence of an elution buffer) and then release the analyte to a down-stream modifying site MS (using a buffer compatible with the operation of the enzyme in the modifying site MS). A final requirement is that experimental artifacts are eliminated from the analysis. Specifically, artifacts arising from enzymologies/ chemistries performed on the analyte on the modifying site MS can, if unchecked, dominate MALDI-TOF mass spectra, essentially suppressing signals from the analyte (especially when the analyte is present in low amounts). To this end, surface-immobilized enzymes are used to provide high enzyme/substrate ratios and to eliminate autolysis fragments from mass spectra.

The outcome of the modifying site MS are modified analytes/fragments whose masses obtained via MS can be used in the structural characterization of the analyte (i.e. protein). This includes protein identification, sequence verification, recognition of conformational difference in proteins, and domain elucidation through serial mapping. Protein identification via mass spectrometry has evolved, quite successfully, to the process of searching genome/protein databases using the masses of peptide fragments resulting from the proteolysis of an analyte (generally fractionated using SDS-PAGE/2D gel electrophoresis) by a specific protease. Protein identification using BCMS can be accomplished through the implementation of the same procedure. A database search using the peptide map shown in FIG. 9, successfully matched human IL-1α as a tenth ranked protein among 618 entries selected when the data was applied to proteins in the mass range of 9.0–36 kDa. However, the matched protein was an IL-1α precursor molecule, with a molecular mass of 30606.8 kDa. When the search criteria were narrowed (MS range of 30–31 kDa), IL-1α was matched as a second ranked protein out of 36 entries selected.

Another use for the bioactive probes is that of mass mapping to detect point mutations in proteins due to genetic polymorphisms or to elucidate sites of chemical modification within proteins due to factors such as chronic exposure to hazardous environments. The detection of the point mutations at the protein level, by accurately determining the mass shift of select proteolytic fragments has significant use in the clinical assessment of ailments typically screened for at the gene level. In either case, mutations/modifications are detected at the protein level, and thus take into account all factors (transcription, translation, enzymatic processing) contributing to the relative abundance of the protein.

A particular advantage of the bioactive chip BC is that it can possess a plurality of different individual action sites, SS-PS-MS, thus creating an array of action sites thereby allowing multi-mode processing and analysis of a sample. On the bioactive chip BC according to the present invention are at least one first action site, the separation sites, SS, that are used to isolate, by methods including but not limited to affinity-capture and adsorption, a specified analyte from an analytical solution. There are at least one second action site, the processing sites, PS, which are used for any additional processing subsequent to the step of isolation. Processing may be accomplished by techniques, including but not limited to, solvent exchange to prepare the analyte for analytical modification, denaturing, or reduction. There is at least one third action site, the modifying sites, MS, which are derivatized with enzymes capable of analytically modifying the analyte.

The separate action sites SS-PS-MS are in fluid contact with each other. Preferably, according to the present invention, the sites are connected by a microfluidics system that includes fluid flow channels, micropumps, and microvalves. The microfluidics system is activated by electrical or pneumatic contacts manufactured in the microfluidics systems according to means well known in the area of microfluidics manufacturing. Thus, an integrated lab-on-a-chip design is produced. More specifically, such multi-mode bioactive chips BC, according to the present invention, may employ a sophisticated miniaturized integrated microfluidics cartridge. Samples and reagents are delivered to the bioreactive chip surface in regulated low volumes by fully automated delivery flow system.

A variety of techniques may be employed to fix interacting and reactive species to the surface of the action sites SS-PS-MS of the bioactive chip BC. Preferably, the interacting or reacting species are directly (covalently) immobilized to the their respective sites. Chips surfaces matrices such as hydrogels of polysaccharides or polymeric amines affixed to a metal surface may be used in the immobilization process. Alternatively, bare metal surfaces with short functionalized linker layers may be used in immobilizing interacting and reacting species. In general, the choice of immobilization chemistry is highly dependent on the object of the action site, and is typically optimized empirically.

During BCMS, the analyte-containing solution is routed across the surface of the bioactive chip BC and allowed to remain in contact with each of the action sites, SS-PS-MS, for various amounts of time. Preferably, SPR is used to monitor interactions and fluid transport. Once all desired interaction analyses and analyte modifications have been performed, the bioactive chip BC is removed from the IA biosensor and molecules contained within areas within the any of the action sites, SS-PS-MS, may be analyzed using identification techniques, such as MALDI-TOF MS. It is important to note that only the first and third action sites SS and MS are absolutely critical to the present invention. The processing action site, PS, is included for the additional benefits that further processing of the analyte creates.

SS—Separation Sites

As depicted in FIG. 1, there are at least one first action site, the separation sites, SS, which accomplish isolation, or separation, of the target analyte, particularly by methods such as affinity capture, adsorption, or the like. Isolation is performed using at least one separation or isolation action site, SS, but may be accomplished using multiple separation sites SS, either in series or in parallel. The isolation or fractionation is preferably accomplished following protocols typical associated with SPR-BIA. The separation sites SS can be used repetitively to determine binding constants between the interacting species, or to capture a maximum amount of sample. Only after the desired amount of analyte or all SPR-BIA data pertinent to the interaction is gathered, will analyte be directed into at least one second action site, the processing sites PS or the modifying sites MS.

It is important to note that it is critical while performing BCMS, to efficiently fractionate a target analyte from a bulk solution. Since the separation site SS a two-dimensional surface of limited capacity, the ability to capture the analyte is highly dependent on the probability of contact between the analyte and the receptor immobilized on the surface of the separation site SS. Regarding the experimental design, immobilized interactants density, flow rates over the separation site SS and buffer composition all affect the efficiency of retrieving an analyte from solution.

PS—Processing Sites

As depicted in FIG. 1, there are at least one second action site, the processing sites, PS, which accomplish additional processing, including but not limited to, buffer exchange, denaturation, reduction, and the like. The rationale for inclusion of the processing step is that the conditions needed to break receptor-analyte interactions on the separation site SS are generally not favorable for "downstream" enzymatic digestion of the analyte in a modifying site MS; most modifying enzymes operate in a buffer range (pH or ionic strength) outside the buffer range generally required and used to disrupt affinity interactions. This difference in buffer ranges frequently requires a buffer exchange. However, the processing site PS is not necessarily used (see Example 8, FIG. 9) or may form only a part of the flowing solution pathway. Additionally, there may be multiple processing sites PS used either in series or in parallel.

Preferably, buffer exchange in the processing sites PS proceeds in one of two manners; either by actively capturing the analyte using a universal media or by scavenging/exchanging unwanted buffer components from a flowing solution. RP-HPLC moieties can be used to accomplish the former of the two approaches. Standard NHS or NHS/EDC chemistries may be employed to immobilize these compounds to the surface of the processing sites PS (e.g., binding octadecylamine to an NHS-activated surface). More specifically, this may be accomplished by derivatizing the processing sites PS with short- to mid-length alphatic chains (i.e., $C_4$–$C_{18}$). In this manner, protein-based analytes will be captured in the processing sites PS while unwanted buffer compounds are rinsed clear. Afterwards the analyte can be eluted into subsequent action sites (i.e. the modifying site MS) using a co-solvent system. The use of co-solvent (such as acetonitrile/aqueous buffer) systems on bioactive probes have been explored and reasonable enzymatic activity has observed using solutions containing up to 40% acetonitrile.

The second method of buffer exchange, solvent exchange, can be viewed as scavenging unwanted buffer components from solution by pre-loading the processing sites PS with an appropriate ion-exchange surface. In this scenario, as the analytical solution, now at a low pH (~2–3, to elute the analyte from the receptor on the separation site SS), is flowed across the processing sites PS, unwanted species in solution are replaced with the appropriate compounds from the ion-exchange surface. This approach is similar to one used to free urine of high salt in order to achieve ion signal in quantitative MS MALDI-TOF MS analyses.

An additional observation supporting the concept of using an ion-exchange process to adjust buffer conditions is that it is necessary to use low pH (~1) matrix solutions to achieve consistent ion signal during MALDI-TOF MS performed on the surface of the bioactive chips BC. In general, a sporadic signal is observed when the matrix is not acidified. Since a bioactive chip BC surface typically consists of gold layer with carboxylated dextran (cation exchanger), it is speculated that a cation exchange process occurs during matrix application. Hydrogen ions in solution are replaced with $Na^+$ (the running buffers are generally high is sodium salt, i.e., the carboxyl groups are loaded with $Na^+$) essentially raising the pH and salting-out a portion of the matrix. MALDI matrices tend to lose function towards neutral pH, which explains the sporadic ion signal. If the ion exchange effect is true, it can be used to adjust the pH of elution buffer to that appropriate for enzymatic activity. Alternatively, it should be possible to use the ion exchange surface in a limited capacity for the same purpose as the RP-HPLC media (i.e., analyte capture). It is proposed that the buffer adjustment can be accomplished by derivatizing the processing site PS with ion exchange moieties (quaternary amine or sulfonyl) by using familiar chemistries.

In order for the processing sites PS to function properly, it is necessary to amplify the surface area of the processing site PS beyond that of other action sites, SS and RS, provided by a typical bioactive chip BC according to the present invention. To date, the preferred surface of the bioactive chips BC are essentially a hydrogel layer comprised of non-crosslinked carboxymethylated dextran. The depth of the layer is preferably ~100 nanometers, which is ideally suited for SPR analyses (in which the maximum SPR penetration depth is ~300 nanometers). However, a substantially thicker layer of hydrogel is necessary to increase the retention or exchange capacity of the processing sites PS. Thus it is proposed to derivatize the processing sites PS with an amplifying media prior to derivatization with the active exchange components. Presently, it is believed that the most reasonable amplification media to be a cross-linked high molecular weight carboxylated dextran or a high molecular weight poly-lysine. Both media result in the surface being amplified with functional groups (carboxyl and amine) from which subsequent derivatization chemistries can be performed. Other moieties, such as agarose or polyacrylamide, may serve in the role of surface amplification.

MS—Modifying Sites

As depicted in FIG. 1, there is at least one third type of action site, a modifying site MS that is used for modifying the analyte. Modification can be by techniques such as enzymatic digestion or processing of the analyte, but is not limited to these techniques only. It has been found that various different combinations of enzymes work well in these sites, separately or together depending on the particular application. Alternately, the analyte may be captured at the modifying site MS and modified by flowing a reacting moiety across the modifying site MS. Additionally, there may be multiple modifying sites MS used either in series or in parallel.

In regard to enzymatic processing, the bioactive chips BC offer the benefits of artifact-free enzymatic mapping of proteins, and zero sample loss due to the transfer of proteolytic digest mixtures. Moreover, when used properly (e.g., with the correct buffer composition and temperature) the bioactive chips BC are capable of very rapid mapping of proteins (5–30 minutes, including mass analysis). These characteristics make the bioactive chips BC attractive means for mass mapping proteins for the presence of point mutations—recognized by the mass shift of proteolytic fragments containing the mutation.

The bioactive chips BC are capable of supplying information, in the form of a sequence tag, for use in database search for protein/gene identification. Dual function bioactive chips BC capable of both mapping and ladder sequencing can be assembled through the immobilization of both an endo and exo-protease on the surface of the modifying site MS. The strategy of preparing an analyte for digestion, such as ladder digestion, using an exopeptidase, by first performing a limited endoproteolytic digestion, works with a high degree of success in generating data used in database search. The rationale behind the strategy is that during database search it is not essential that the sequence data originate from the termini of the protein. Thus, limited endoproteolysis results in a number of starting fragments on which an exoprotease can work. With the increased number of starting fragments comes an increase in the odds that the endoprotease will generate ladder sequence pertaining to the intact molecule.

Since the object of the mapping digest is to prepare analyte for ladder sequencing, the enodoprotease does not have to be highly specific. Thus α-chymotrypsin and pepsin can be used to prepare analyte for sequencing with aminopeptidases and carboxypeptidases, respectively. The two enzyme combinations are chosen because they exhibit similar pH ranges of operation; α-chymotrypsin/aminopeptidases working at pH~8; pepsin/ carboxypeptidases operating at pH~3. In this manner, a single solvent system can be employed for both the endo- and exopeptidase. All of these enzymes have been immobilized on modifying sites MS to create bioactive chips BC with reasonably high activity. These combinations of enzymes are used to demonstrate the universality of performing the mapping/sequencing operation in the bioactive chip BC.

Single digest mass mapping can be used for protein identification by virtue of the specificity of the enzyme and accurate mass determination of the fragments (the data used in database search). The use of a trypsin-active action site capable of protein identification through mapping is shown in Example 7. Endoproteases Lys-C, Asp-N, Arg-C and Staph V8 can be used for similar applications and also to prepare mass maps for the aforementioned partial sequencing. Beyond mapping for sequence verification/identification, mapping is used to investigate higher-order protein structures. In this application, mapping is used to evaluate the accessibility of potential cleavage sites to an enzyme. The mapping process is generally performed in the relative sense (e.g., with maps taken of a protein exposed to different environments) and the results compared to evaluate difference in cleavage pattern brought on by differences in structure. Such comparative mapping, using bioactive chips BC, is used to recognize differences in protein structure due to the presence of allosteric effectors, denaturants, and coordinated metal ions (e.g., apo or holo zinc fingers).

Another form of cleavage analysis is that of cleaving post-translationally added groups from proteins using the enzymes. Examples of enzymes for this purpose include, but are not limited to, phosphatases and glycosidases, for the cleavage of phosphates or sugars moieties from proteins, respectively.

Alternatively, enzymatic or chemical modification can be used to add characteristic functional groups to analytes. Such enzymes/chemicals include, but are not limited to, kinases, methyl-transferases, iodoacetimide, and the like. These addition modifications are beneficial to analysis in "tagging" specific amino acid residues or motifs, as well as enhancing the analytical performance of the target analyte during mass spectrometry.

In the practice of this invention, the bioactive chip BC is employed to perform real-time analysis. Although IA provides pertinent information on analyte binding and kinetics, identity of the analyte(s) is dependent on the specificity of the receptor and may not always be certain. This is particularly true in complex systems where there exists the potential to bind multiple or unknown analytes, either nonspecifically or in competition for the surface bound receptor. Such nondefined binding is of significant concern. By mass spectrometrically analyzing retained analytes it is possible to detect the presence of nontargeted analytes (with high sensitivity), and to correct for them using quantitative techniques.

To avoid transfer losses and achieve the best sensitivity, analytes are preferably sampled directly from the bioactive surface rather than eluted into a mass spectrometer. However, alternative sampling techniques including but not limited to subsequent elution to an electrospray unit are considered to fall within the scope of the present invention. In short, the bioactive probe, according to the present invention, is preferably employed as a sampling stage for MS. The location of the ion signal on the mass spectrum is dependent upon the molecular mass of the analyte (i.e., the mass-to-charge ratio), thereby identifying the analyte. The mass spectral signal also has magnitude (i.e., height of the signal or area under the same). The magnitude of the signal is indicative of the amount of analyte that is ionized and detected by the mass spectrometer. Suitable mass spectrometers include, but are not limited to, a magnetic sector mass spectrometer, a Fourier transform ion cyclotron resonance (FTICR) mass spectrometer, a quadrapole (rods or ion trap) mass spectrometer and a time-of-flight (TOF) mass spectrometer. In a preferred embodiment, the mass spectrometer is a time-of-flight (TOF) mass spectrometer.

Depending upon the size and nature of the analyte captured by the bioactive chip BC, a desorption/ionization matrix material may optionally be employed. Since large molecules, such as peptides and proteins, are generally too large to be desorbed/ionized intact, a matrix is used to assist laser desorption/ionization of the same. This technique is referred to as matrix assisted laser desorption/ionization or (MALDI), and the matrix agent is referred to as a "MALDI matrix." In short, the captured analyte on the bioactive chip BC is contacted with a suitable MALDI matrix and allowed to crystallize on the bioactive chip BC by, for example, air drying. Suitable MALDI matrix materials are known to those skilled in this field, and include, for example, derivatives of cinnamic acid such as a-cyano-4-hydroxycinnamic acid (ACCA) and sinapinic acid (SA). Suitable methods for applying the matrix on a bioactive chip BC are manual application through a pipette, delivery through piezoelectric "ink" jets, or painting using a mechanical applicator. However, the preferred method is application of the matrix as an aerosol. In this method, an aerosol applicator, consisting of an aspirating/sheath gas needle (~30 µm orifice) backed by compressed air, is used to produce a fine mist of matrix solution. Upon spraying, the entire bioactive chip BC surface is covered with fine drops of matrix solution that stay separated from each other. The matrix solution is acidified (pH~2, containing 0.2% trifluoroacetic acid) and thus, in the case of the separation site SS, able to break the receptor-analyte interaction effectively desorbing the affinity-retained analytess from the surfaces, or in the case of the modifying site MS, is able to effectively incorporate the modified analyte into the matrix. Upon rapid drying, the matrix/analyte mix is redeposited on the action site on which the analyte was present. The resulting homogeneous matrix/analyte layer allows acquisition of repetitive and reproducible spectra over the entire area of each action site. Moreover, spatial resolution between the action sites on the bioactive chip BC is maintained during the matrix application.

A first criterion to performing mass spectrometry on the analyte captured by the interactive surface is the generation of vapor-phase ions. In the practice of this invention, such species are generated by desorption/ionization techniques. Suitable techniques include desorption/ionization methods derived from impact of particles with the sample. These methods include fast atom bombardment (FAB impact of neutrals with a sample suspended in a volatile matrix), secondary ion mass spectrometry (SIMS impact of keV primary ions generating secondary ions from a surface), liquid SIMS (LSIMS—like FAB except the primary species is an ion), plasma desorption mass spectrometry (like SIMS except using MeV primary ions), massive cluster impact (MCI—like SIMS using large cluster primary ions), laser desorption/ionization (LDI—laser light is used to desorbed/ionize species from a surface), and matrix-assisted laser desorption/ionization (MALDI—like LDI except the species are desorbed/ionized from a matrix capable of assisting in the desorption and ionization events). Any of the aforementioned desorption/ionization techniques may be employed in the practice of the present invention. In a preferred embodiment, LDI is employed, and in a more preferred embodiment, MALDI is utilized.

With regard to MALDI, laser energy is impinged upon the surface of the bioactive chip BC, resulting in the desorption/ionization of the captured analyte. The ionized analyte is then detected by the mass spectrometer. In one embodiment of this invention, the laser is directed to the surface of the bioactive chip BC having the analyte captured thereon. In an alternative embodiment, the laser may be directed to the backside of the bioactive chip BC. In the case of a transparent bioactive chip BC, the laser may be directed through the transparent material such that it strikes the backside of the metal layer in contact with the captured analyte.

Furthermore, when multiple active sites, SS-PS-MS, are employed on a single bioactive chip BC, the laser may be directed to a single active site at a time. In this manner, the captured analyte from the single site may be analyzed by mass spectrometry. When the desired mass spectral data has been collected from a particular site, the laser may then be directed to the next site for analysis. In this manner, the mass spectrum of analytes captured by the active sites may be individually addressed. This is particularly advantageous when each of the interactive sites provides different information concerning the analyte or analytes within the sample, or provides further confirmation that the analyte is present within the sample of interest.

In all, BCMS is a concerted analysis useful for the investigation of interactions between biomolecules, and used to detect/quantify/identify biomolecular recognition events (and handle samples) at trace levels. Critical to the success of the BCMS are the following: the ability to perform different operations (affinity capture, post separation processing, or enzymatic treatment) on different action sites on the bioactive chip BC, and spatially resolve the different actions sites throughout the entire process; the use of IA (preferably SPR) and MS (preferably MALDI-TOF) to analyze multi-component affinity systems; achieving high specificity and sensitivity analyses when targeting analytes present in complex mixtures; correcting quantitative SPR-BIA estimates for heterogeneous/competitive binding systems; and accurately determining the site and nature of point mutations in proteins resulting from genetic polymorphisms.

The following examples illustrate the fundamental chemistries and enzymologies needed to perform BCMS analyses on a bioactive chip BC, as the arrangement (order) and use of action sites is dependent on the particular analysis and the specific analyte.

EXAMPLE 1

Separation Site SS

Figures 2A, 2B, 2C:
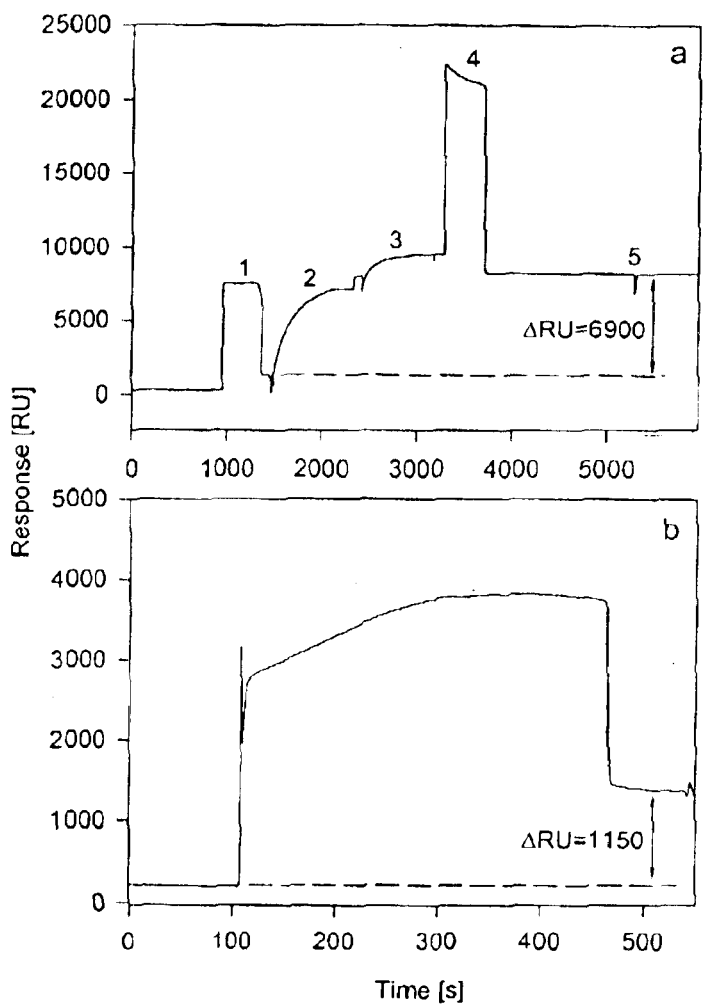
FIG. 2 illustrates the performance of a separation site SS on a bioactive chip BC (a) Sensorgram of anti-human immobilization IL-1α on the separation site SS by (1) EDC/NHS chip surface activation, (2,3) antibody linkage, (4) ethanolamine blocking and (5) ammonium citrate (pH 2.5) rinsing. An overall response change of $\Delta RU=6900$ indicates the covalent immobilization of ~46 fmoles of antibody (maximum valence ~92 fmole). (b) Sensorgram of IL-1α affinity capture in the separation site SS. The response change indicates the retention of ~60 fmole of IL-1α. (c) MALDI-TOF mass spectrum taken directly from the surface of the separation site SS on which IL-1α was captured. Signals consistent with the retention of intact and a truncated version of IL-1α are observed, as well as an unknown peptide signal (*). The spectrum is the sum of ~50 laser shots using a MALDI matrix of ACCA.

In this example, capture of IL-1α on a separation site SS and subsequent MALDI-TOF mass spectrometry performed directly from the separation site SS on a bioactive chip BC is shown. FIG. 2a shows a sensorgram of anti-IL-1α antibody immobilization on the separation site SS. The response change of 6900 RU indicates the immobilization of 6.9 nanograms of material, which corresponds to ~46 fmoles of antibody ($MW_{IgG}$~150,000) immobilized (maximum valence ~92 fmole). FIG. 2b shows a sensorgram of the subsequent capture of IL-1α ($10^{-4}$ mg/mL, in large excess (10 mg/mL) of human serum albumin, HSA). A response change of 1150 RU indicates the retention of ~1.15 nanograms of proteinaceous material (~60 fmole of IL-1α). FIG. 2c shows a MALDI-TOF mass spectrum taken from the surface of this separation site SS. The observed m/z values of 18038 Da, 9021.7 Da, and 6017.2 Da correspond to the singly, doubly and triply charged ions of IL-1α and are in good agreement with the calculated mass of IL-1α ($MW_{recombinant\ human\ IL-1\alpha}$=18047.5). A second, less intense, series of signals indicate the presence of a species at MW=17,390, presumable due to a truncated version of the IL-1α (loss of six amino acids from the N-terminal). Neither signals for HSA nor the antibody were observed in mass spectra taken from the surface of the separation site SS or regions on the bioactive chip BC bordering the separation site SS.

EXAMPLE 2

Separation Site SS: Optimization of the Flow Rate

Figure 3:
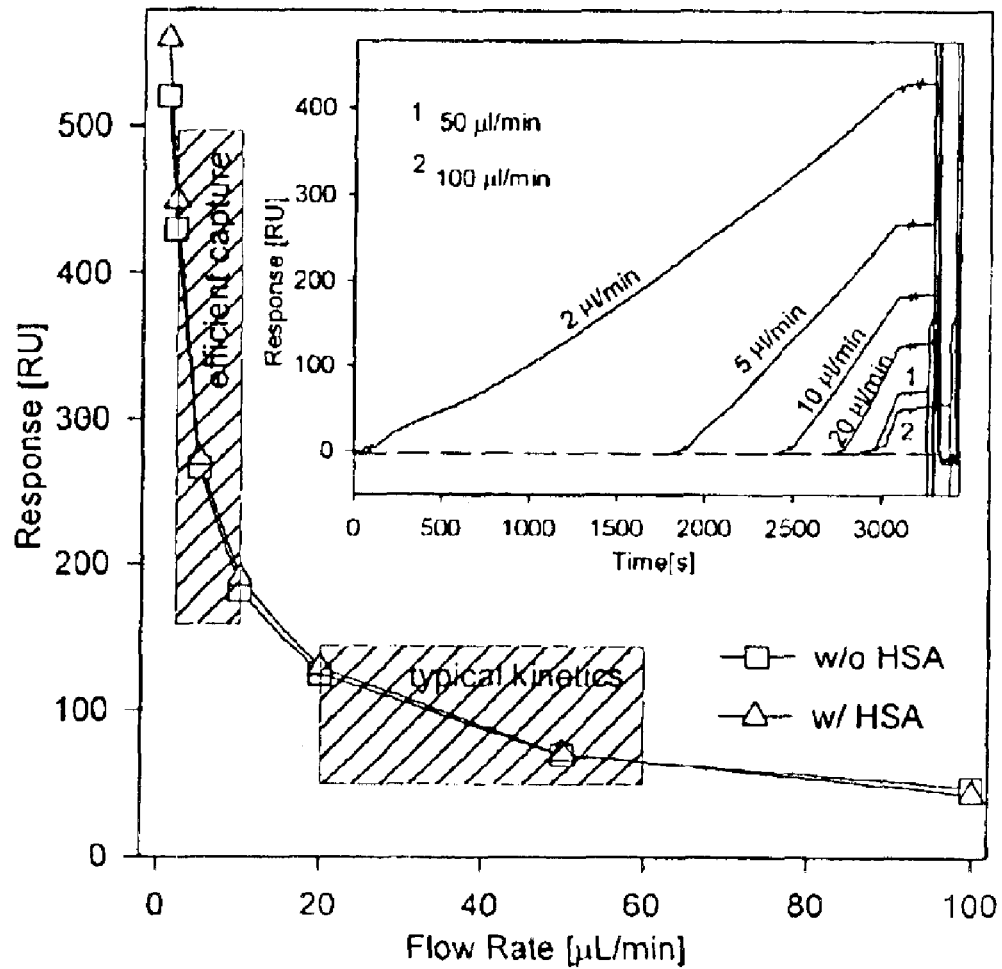
FIG. 3 illustrates the dependence of the capture efficiency on the flow rate over the separation site SS on a bioactive chip BC. The responses from the binding of human IL-1α to the anti-IL-1α-derivatized separation site SS were plotted vs. the corresponding flow rates (the sensorgrams showing binding of IL-1α at different flow rates are shown in the inset). The capture efficiency increases geometrically with decreased flow rates.

In an example of separation site SS optimization, mouse monoclonal anti-human interluken-1 alpha (anti-IL-1α) was immobilized on a separation site SS on a bioactive chip BC using an amine-coupling procedure (as shown in the previous example). 100-μL aliquots of solutions containing human interleukin-1α (IL-1α) were injected over the separation site SS at various flow rates. A low analyte concentration ($10^{-5}$ mg/mL IL-1α, with and without 10 mg/mL human serum albumin (HSA, carrier protein) in HBS) was used in this example to avoid saturation of the immobilized anti-IL-1α (SPR response at saturation; ΔRU=1600). The binding curves shown in FIG. 3 (inset) show increased binding at decreased flow rates, indicating that the efficiency of retrieval increases geometrically as the flow rate is decreased. At the lowest flow rate examined (1 μL/min), ~31 fmoles of IL-1α were captured, equating to a capture efficiency of approximately 56% (55 fmoles of Il-1α were contained in each 100 μL injection).

One of the things this experiment demonstrates is the benefit of using low flow rates for efficient analyte capture in the separation site SS. Methods generally employed in SPR-based biosensor operations typically utilize higher flow rates because most interaction analysis experiments are performed for studying the kinetic parameters of various biomolecular interactions and therefore require utilization of low receptor densities and high flow rates in order to avoid deviations resulting from mass transfer. However, under the conditions of the present invention, low flow rates are preferred allowing analyte re-capture on the same separation site SS and maximized diffusion within the separation site SS, as a result of which more efficient analyte capture on the separation site SS is achieved. Based on the present studies, the preferred flow rates for using BCMS are 1–5 μL/minute, allowing analyte capture efficiencies of 25–50% (with excess immobilized receptor).

EXAMPLE 3

Separation Site SS: Competitive/Heterogeneous Systems

Figure 4A:
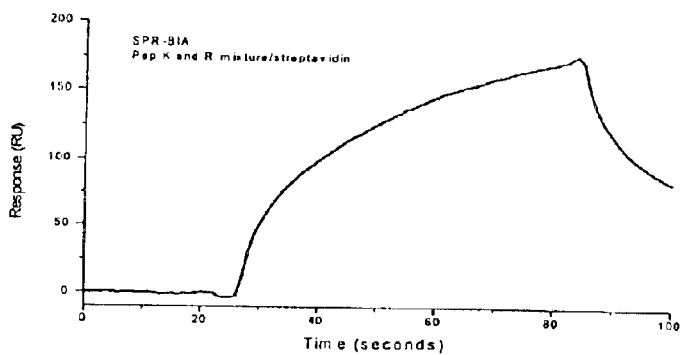
FIG. 4 illustrates BCMS analysis of competitive/heterogeneous systems. (a) Sensorgram of the interaction between PepK and PepR mixture with streptavidin immobilized on a separation site SS of the bioactive chip BC. (b) MALDI-TOF mass spectra taken before (gray) and after (from the surface of the separation site SS on the bioactive chip BC, black) the SPR-monitored interaction. (c) Curve-fitting simulation of the SPR-BIA data obtained by taking into account the semi-quantitative MALDI-TOF MS data.

This example shows the applicability of BCMS in analyzing competitive/heterogeneous analyte systems. FIG. 4a shows a sensorgram of the interaction between streptavidin (immobilized on the surface of separation site SS on a bioactive chip BC) and the recognition sequence—HPQ—contained in the peptides:

SGTSFHPQWIMVGKVATNSP (SEQ ID NO: 1) (Pep K; MW=2203.5 Da), and.

SGTSFHPQWIMVGRVATNSP (SEQ ID NO: 2) (Pep R; MW=2231.5 Da).

Figure 4B:
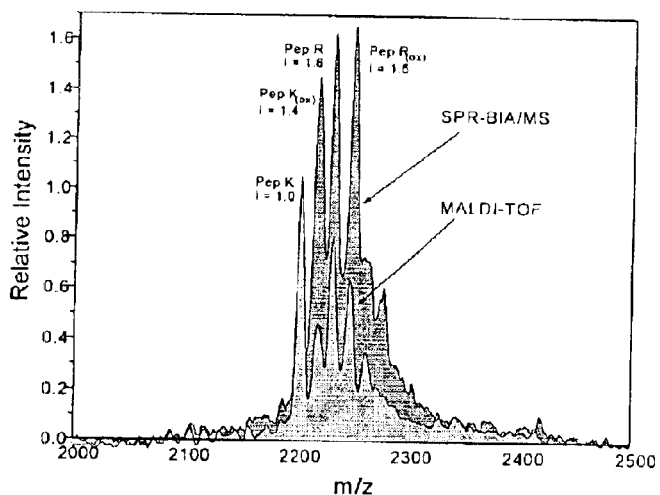

A bioactive chip BC containing streptavidin-derivatized separation site SS was exposed for 60 s (at a flow rate of 20 μl/min) to a mixture containing 10.0 μM Pep K and 10.0 μM Pep R, after which a ~15 s exposure to the running buffer followed. The separation site SS on the bioactive chip BC was then MALDI-TOF MS analyzed. FIG. 4b shows an overlay of two mass spectra resulting from the analysis of the peptide mixture before (MALDI-TOF MS of the analytical solution, grey) and after the interaction analysis (MALDI-TOF MS taken from the surface of separation site SS on the bioactive chip BC, black). The intensity ratio between the two species is observed to change as a result of the affinity interaction analysis, or better put, due to preferential retention of the PepR variant by streptavidin. Oxidized versions of the two peptide variants apparently exhibit an even higher affinity for streptavidin, as indicated by the increase in relative ion signal intensity.

Figure 4C:
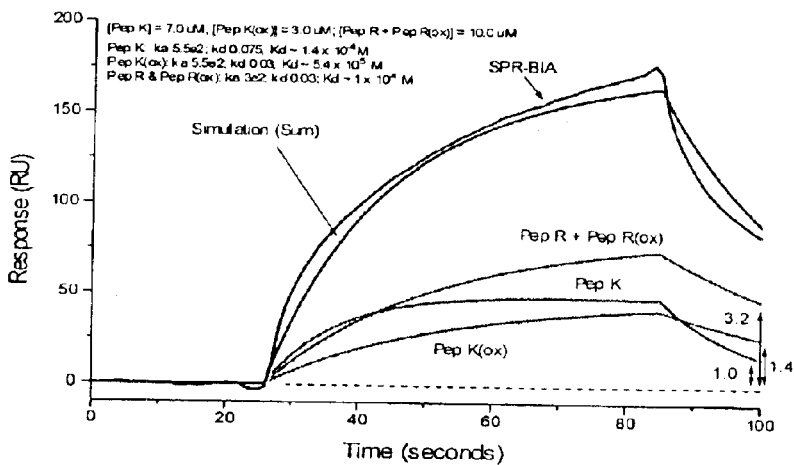

The binding curve shown in FIG. 4a does not differentiate between the binding of the two homologous peptides or their oxidation products. The curve is actually a composite of the binding curves of the individual species. Deriving a single affinity constant from the SPR data is therefore inaccurate because there are at least four species contributing to the curve, each with slightly different affinity. FIG. 4c shows a simulation in which a composite of three separate binding curves are fit to the SPR data (because of software limitations three curves were used instead of four—one curve represents both Pep R and oxidized Pep R). The fitting parameters are listed in the figure and were used with starting concentrations of [Pep K]=7 uM; [Pep K(ox)]=3 uM; and [Pep R & Pep R(ox)]=10 uM. A criterion was used in which the relative quantities of the individual species at the end of the run corresponded to the relative quantities estimated from the mass spectrum taken from the surface of the separation site SS. The fitting is not perfect, but is generally consistent with both the SPR and MS data, and represents a first attempt at using MS data to differentiate the relative contributions of multiple species to a single SPR binding curve.

EXAMPLE 4

Processing Site PS

Figure 5A:
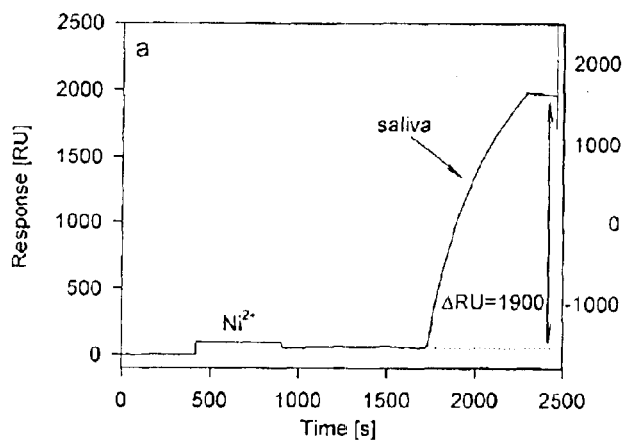
FIG. 5 illustrates a performance of a processing site PS on the bioactive chip BC containing chelating surfaces. Shown are sensorgrams resulting from screening of human whole saliva (diluted 1:100 in HBS) over either an (a) TED/$Ni^{2+}$ or (b) EDTA/$Ca^{2+}$-activated surface. (c) Mass profiles obtained from the surface of the processing sites PS (see text for assignment of species; * unidentified signals).
Figure 5B:
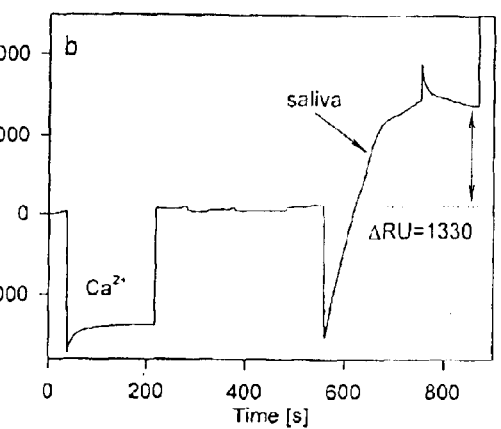
Figure 5C:
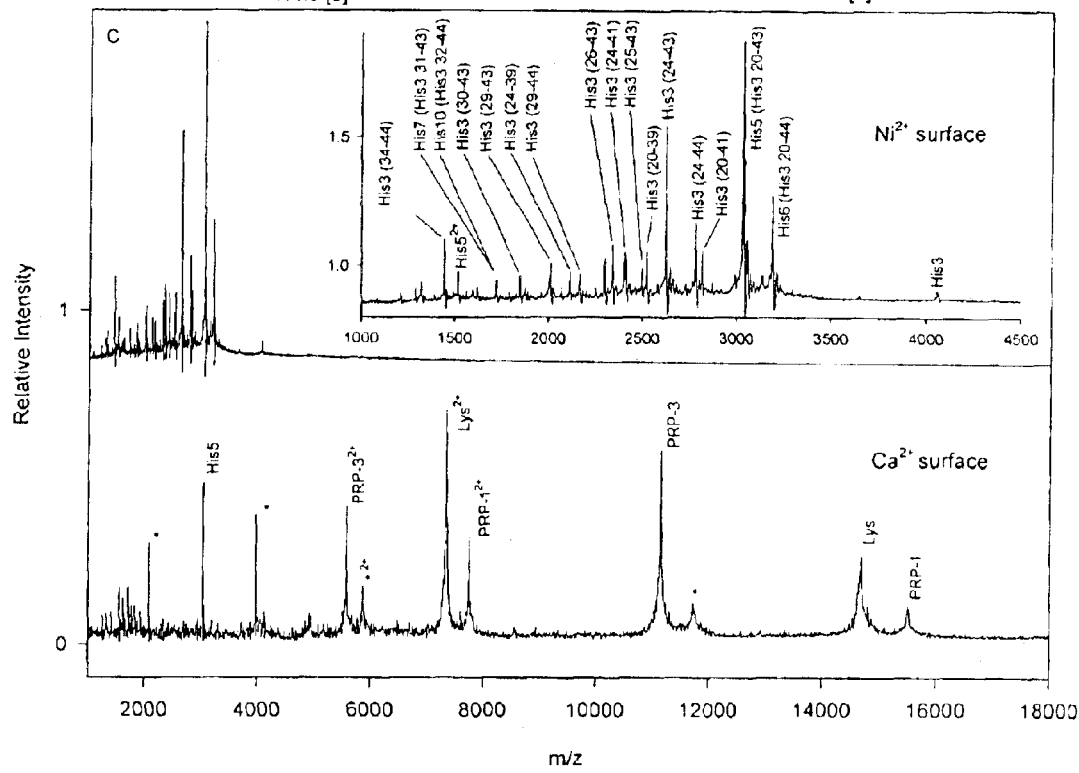

The use of chelators as exchange surfaces for processing sites PS on a bioactive chip BC was investigated in this example. FIG. 5a shows a sensorgram obtained from screening of human whole saliva using a TED/$Ni^{2+}$ chelate sensor surface. The processing site PS surface was prepared using DSP activation (in isopropanol) of the gold (top surface layer of the bioactive chip BC), coupling of 3,3'-iminobispropylamine (DADPA, 1:1:3; DADPA:TEA:IP) to create an amine surface and then conversion to the chelate surface by exposure to EDTA dianhydride (in 100 mM phosphate; pH 5). The DSP activation and DADPA steps were performed outside the SPR biosensor; the conversion to the chelate surface was performed in an aqueous environment inside the biosensor. The TED surface was loaded with $Ni^{2+}$ using a short injection of 20mM $NiCl_2$, immediately prior to the injection of a diluted saliva (1:100 in HBS). A second sensorgram (FIG. 5b) is shown for the screening of the saliva sample using an EDTN$Ca^{2+}$ chelate surface. The surface was prepared as described above, except for using DTPA dianhydride instead of EDTA dianhydride. As with the $Ni^{2+}$ surface, $Ca^{2+}$ was loaded onto the surface of the processing site PS immediately prior to the injection of the diluted saliva. Approximately 1.3–1.9 nanograms of proteinacious material were retained during each of the analyses. MALDI-TOF MS analyses of the processing sites PS (FIG. 5c) show dramatically different spectra, reflecting the surface properties of each processing site PS. Because many salivary proteins have been previously characterized, most of the retained proteins were tentatively identified by their molecular masses. The peptides retained by the $Ni^{2+}$-chelate surface were identified as Histatin 3 (His3) and related enzymatic breakdown products (histatins 4–10, see inset FIG. 5c). All of the peptides share the amino acid sequence—HEKHHSH—(SEQ ID NO: 3), the high histidine content of which serves as $Ni^{2+}$ coordination site. Signals in the mass spectrum obtained from the $Ca^{2+}$-chelate surface can be assigned to salivary PRP-1 ($MW_{calc}$=15,532; $MW_{obs}$=15,520) and PRP-3 ($MW_{calc}$=11,179; $MW_{obs}$=11,170), lysozyme ($MW_{calc}$=14,693; $MW_{obs}$=14,690), and histatin 5 ($MW_{calc}$=3,036.1; $MW_{obs}$=3,035). PRP-1 and -3 are known $Ca^{2+}$ binding proteins, containing between 3 and 7 binding $Ca^{2+}$ sites, and are most probably bound through interaction with the immobilized $Ca^{2+}$ Lysozyme, although not a known $Ca^{2+}$ binding protein, is fairly basic (pI~11) and is most likely retained through ionic interactions with unsaturated carboxyl groups present on the processing site PS. The retention of Histatin 5 is most likely due to its coordination with ambient $Ni^{2+}$ present in the solution, or perhaps through a marginal affinity to $Ca^{2+}$. Considering both the SPR and MALDI-TOF MS data, approximately 10–50 fmol of each protein/peptide is estimated to be retained on the processing site PS on the bioactive chip BC.

One of the things this example illustrates is the potential use of chelate/metal surfaces as processing sites PS during BCMS. In this scenario, chelate surfaces on processing sites PS downstream from separation sites SS would be used to capture analytes (or analyte fragments with certain functionalities) eluted from the separation site SS, after their initial retention by the receptor in the separation site SS. The analytes can then be released from the chelate processing sites PS at a pH appropriate for enzymatic digestion using buffers loaded with competitive small ligands (e.g., immidizole, histidine, phosphate, EGTA or EDTA) which would not prevent enzymatic activity in the downstream modifying sites MS. Similar processing sites PS constructed using $Ga^{3+}$ or $Fe^{3+}$ as the exchanger could find reasonable use in the analysis of phosphorylated peptides.

EXAMPLE 5

A Combination of Separation Site SS and Processing Site PS

In this example, a functional combination and operation of separation site SS followed by processing site PS on a bioactive chip BC was investigated. For that purpose, anti-$β_2$m (beta-2-microglobulin) antibody was immobilized on a separation site SS and the surface of the processing site PS was derivatized with high molecular weight (500 kDa) carboxymethyldextran (serving as cation exchange surface). A continuous flow buffer of 10 mM sodium acetate, pH 5, was used throughout the experiments, with injection buffers/solutions as noted on the figure. In the first iteration (sensorgram, FIG. 6a), flow was directed over only the separation site SS, and the antibody saturated with a 30 μL injection of $β_2$m ($10^{-3}$ mg/mL $β_2$m in HBS). Approximately 370 pgrams of $β_2$m were retained on the separation site SS. Flow was then directed through both action sites, and 80 μL of elution buffer (10 mM citric acid, pH 2.4) injected over both action sites serially. The SPR response from the separation site SS exhibits the general characteristics of an elution profile, whereas the response from the processing site PS takes on the characteristics of protein binding. Readings taken after the end of the elution buffer injection indicate the removal of ~300 pgrams of $\beta_2$m from the separation site SS (~80% elution efficiency) and capture of ~175 pgrams of $\beta_2$m in the processing site PS (~60% capture efficiency). Flow was then returned to the separation site SS, and a second, stronger elution buffer (10 mM ammonium citrate pH 2.2) injected for control purposes (to elute any residual $\beta_2$m from the separation site SS). Flow was then directed over the processing site PS, and a high(er) pH buffer (10 mM borate, pH 10) used to elute the $\beta_2$m from the exchange processing site PS. A final reading indicates the elution of ~115 pgrams (~65% elution efficiency) of $\beta_2$m from the processing site PS (and into a hypothetical trypsin-derivatized modifying site MS). The experiment was then repeated with the exception of the final high-pH elution. Sensorgrams obtained during the repeat (FIG. 6b) show similar results, with ~150 pgram (~12 fmole) of $\beta_2$m present on the processing site PS at the time of removal of the bioactive chip BC from the SPR-instrument. MALDI-TOF mass spectra taken from the surface of the processing site PS confirm the presence of $\beta_2$m on the processing site PS (inset, FIG. 6b), consistent with the general premise of the experiment. As expected, $\beta_2$m was not detected on the separation site SS, due to the HCl and NaOH washes performed in the biosensor following the $\beta_2$m elution from the separation site SS. (FIG. 6b). The overall efficiency of the process (amount eluted from the processing site PS/amount captured in the separation site SS) using the present conditions is ~30%. Even though this number is low, these results are quite encouraging—capture and transfer operations on the <50 fmole level.

One of the things this example demonstrates is the functional and operational combination of a separation site SS with a processing site PS on a bioactive chip BC. In this example, cation exchange surfaces were used for buffer exchange in the processing site PS. The efficiency of the exchange process can be increased by using different buffers for elution/capture and the use of lower flow rates throughout the process (Note: high flow rates (20 µL/min) were used in this experiment due to degraded performance of the microfluidics system). In addition, surfaces with other cation exchange groups (e.g., dextran sulfate and heparin) can be employed and applied to analytes of varying pIs to find optimal cation exchange surfaces. Lastly, the process can be applied in a similar manner for anion exchange processing sites PS.

EXAMPLE 6

Modifying Site MS: Mapping for Point Mutations

This example shows the use of trypsin bioactive probes to recognize a point mutation in the (human) serum transport protein transthyretin (TTR):
GPTGTGESKCPLMVKVLDAVR GSPAINVA(V/M) HVFRKADDTWEPFASGKTSESGELHGLTTEEEFVE GIYKVEIDTKSYWKALGISPFHEHAEWFTANDSG PRRYTIAALLSPYSYSTTAWTNPKE (SEQ ID NO: 4)
(Point mutation shown in bold; the T4 proteolytic fragment is double underlined; the protein is heterogeneous due to multiple oxidation products at Cys10). Sequence variants of TTR have been linked to the formation of protein (amyloid) fibrils in tissues and around nerves, leading to a number of ailments including autonomic neuropathy, amyloidotic cardiomyopathy, carpal tunnel syndrome and degenerative liver disorders.

Figure 7:
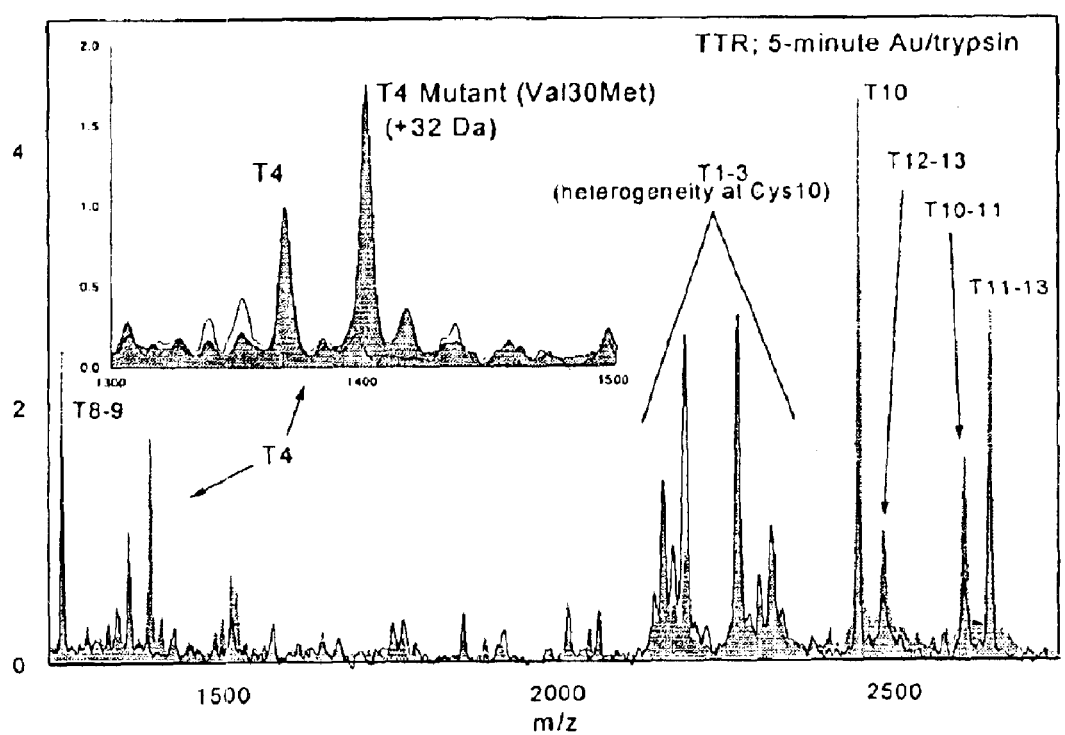
FIG. 7 illustrates the applicability of a modifying site MS on a bioactive chip BC in mapping for point mutations. Shown are MALDI-TOF MS spectra of two tryptic digests of human transthyretin (TTR) from modifying sites MS on a bioactive chip BC: one of the wild type (outline) and the second of a mixture containing the wild type protein an a mutant containing the Val30Met point mutation (grey). A signal at m/z=1400 is consistent with the +32 Da mass shift of the T4 proteolytic fragment in the mutant form.

Two MALDI-TOF MS tryptic maps are shown in FIG. 7: one of normal TTR (outline) and one of a mixture of TTR and TTR possessing a point mutation significant to liver disorder—Val30Met (gray). The maps show a high degree of similarity with the exception of a signal at m/z=1400 Da unique to the map of the mutant. The signal is due to the addition of 32 Da (the difference in mass between Val and Met) within the T4 proteolytic fragment.

One of the things this example demonstrates is the use of bioactive chips BC to evaluate point mutations in proteins. It should be noted that the analyses were performed rapidly (5-minute digest; ~15 minutes for total analysis), and required ~0.5 pmole of analyte. It is also worth noting that the mass map showing the signal due to the mutant protein was the product of a mixed population of both wild and mutant proteins—i.e., showed signals consistent with both variants (wild and mutant) of the protein. Such ability is considered critical when tracking the progression of degenerative disorders related to the progressive increase of mutant proteins. Also, analysis at the protein level allows the detection of mutations due to not only gene defects, but also mutations due to exposure to different environments (e.g., heterogeneity of oxidative group on Cys10—see FIG. 7).

EXAMPLE 7

Modifying Site MS: Bioactive Chip BC Digest Using Trypsin

Figure 8A:
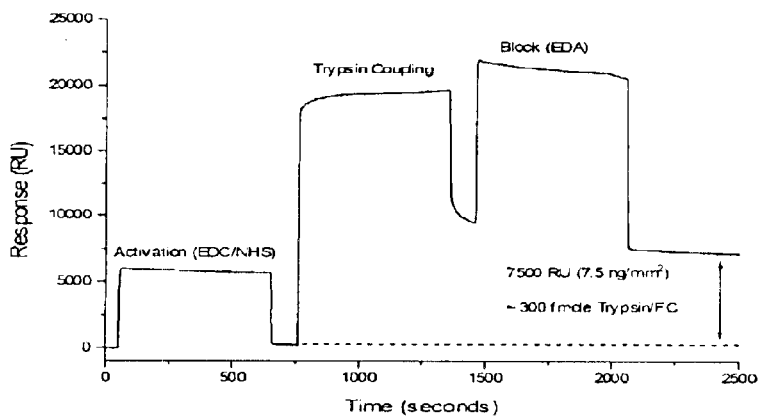
FIG. 8 illustrates the performance of a trypsin-derivatized modifying site MS on a bioactive chip BC. (a) Sensorgram showing the covalent immobilization of trypsin on the modifying site MS. (b) (SEQ ID NO: 5) Sensorgram monitoring the diges ion of $\alpha$-cobratoxin on the modifying site MS on the bioactive chip BC. (c) Mapping MALDI-TOF mass spectrum taken from the surface of a bioactive modifying site MS following the trypsin digestion. Coverage maps are shown indicating the N/N version of $\alpha$-cobratoxin.
Figure 8B:
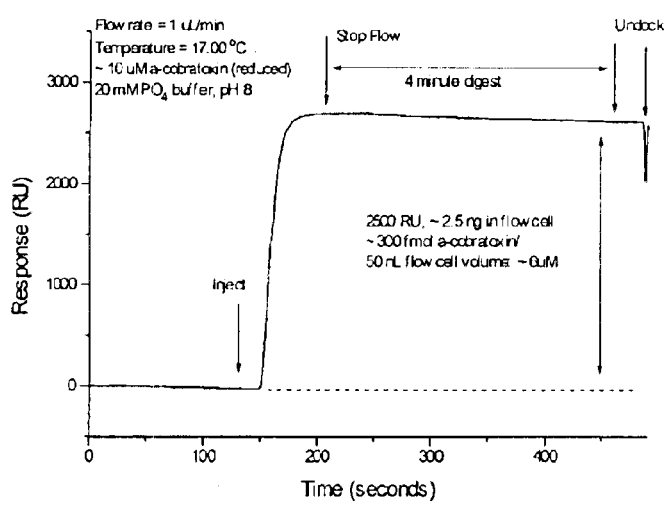
Figure 8C:
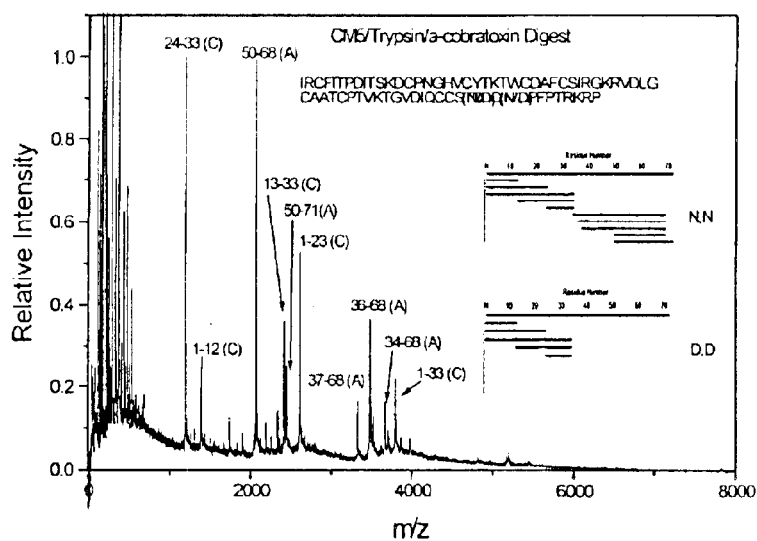

FIG. 8a and FIG. 8b show, respectively, sensorgrams taken during the immobilization of trypsin to a modifying site MS on a bioactive chip BC, and the subsequent digest of α-cobratoxin inside the modifying site MS. In general, an enzyme-to-substrate ratio of ~1 (~300 fmole of both enzyme and analyte) was used during the 4 minute, 17° C. digest of the toxin. The mass spectrum taken from the modifying site MS shows proteolytic fragments characteristic of the toxin, and a complete absence of autolytic fragments of the trypsin (FIG. 8c). Mass accuracy, using self-consistent internal calibration, was sufficient to elucidate two N/D discrepancies with the SWISSPROT database.

EXAMPLE 8

A Combination of Separation Site SS and Modifying Site MS

Figure 9A:
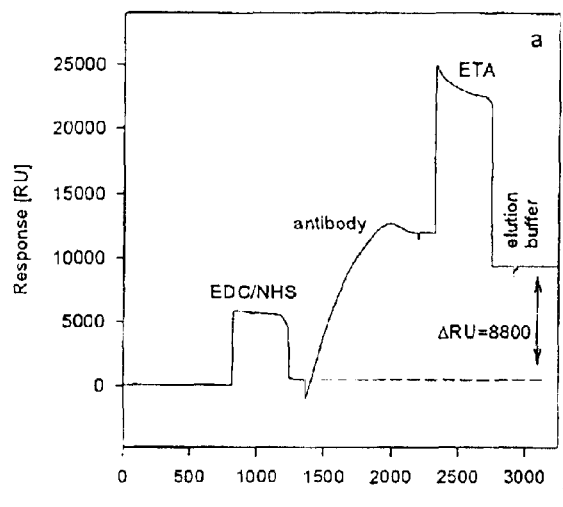
FIG. 9 illustrates the functional combination and operation of separation site SS and modifying site MS on a bioactive chip BC. (a) Sensorgram of anti IL-1$\alpha$ immobilization on the separation site SS. (b) Sensorgram of pepsin immobilization on the modifying site MS. 3,3' iminobispropylamine (10% v/v in water, pH~12) served as an amino linker to which pepsin (0.5 mg/mL, with 0.2 mM EDC and 5.0 mg/mL with 0.2 mM EDC, both in 10 mM phosphate, pH 5.7) was consequently immobilized, utilizing 10 mM phosphate, pH 5.7 as a running buffer. (c) Sensorgram showing IL-1$\alpha$ capture in the separation site SS, elution from the separation site SS and routing into the modifying site MS, and digestion in the pepsin-active modifying site MS. IL-1$\alpha$ ($10^{-4}$ mg/mL, in HBS-EP, containing 10 mg/mL HSA) was injected at 5 $\mu$L/min with 10 mM phosphate, pH 5.7 as a running buffer. During capture, flow through was directed only through the separation site SS. After the capture, the flow was directed through both action sites and after a short rinsing period (at flow rate of 10 $\mu$L/min), the flow rate of the system was reduced to 1 $\mu$L/min. One microliter of a pH 2.5 elution buffer was then injected over the action sites and progress through the system was monitored in real-time using SPR. Once the sample-carrying elution buffer entered the modifying site MS, flow was stopped and approximately 6 minutes was given for digestion of the analyte. The subsequent MALDI-TOF analysis (d) yields masses of the IL-1$\alpha$ peptic fragments that are in good agreement with the IL-1$\alpha$ (sequence (inset).
Figure 9C:
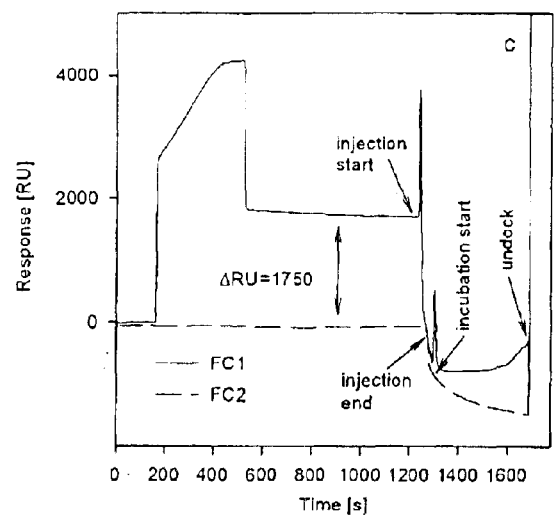
Figure 9B:
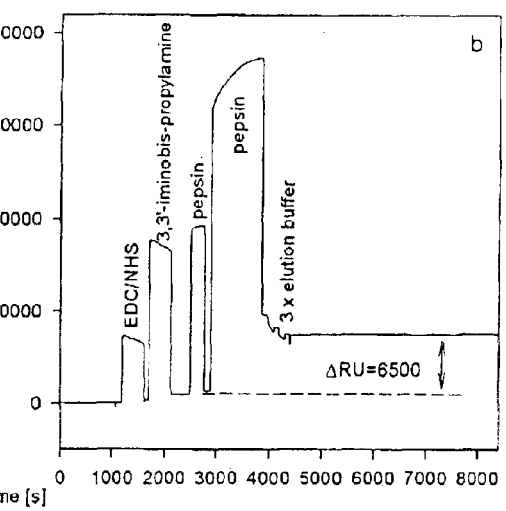
Figure 9D:
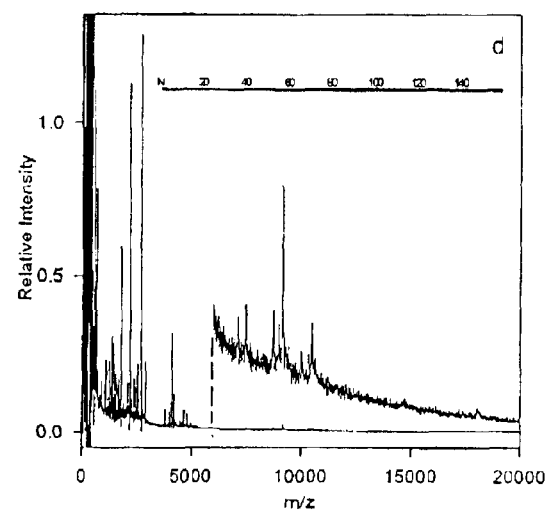

FIGS. 9a and 9b show sensorgrams of the immobilization of anti-IL-1α antibody on a separation site SS on the bioactive chip BC and immobilization of pepsin on a modifying site MS on a bioactive chip BC, respectively. The SPR responses observed in the two sensorgrams correspond to ~8.8 nanograms (~59 fmoles) of antibody immobilized on the separation site SS (~118 fmoles valence) and 6.5 nanograms (~190 fmoles) of pepsin immobilized on the modifying site MS. Noted is the use of 3,3'-iminobis-propylamine in the surface activation procedure for the pepsin immobilization. Attempts to immobilize pepsin through the EDC/NHS protocol (using an amine-targeted linkage) failed to provide surfaces with enzymatic activity. The reason for this shortcoming is the low pI of the enzyme, the enzyme has few free amines for immobilization and is repelled by the negative charge of the carboxylate surface of the sensor chip. Switching to the amine surface resolves this problem and results in high densities of immobilized enzyme. FIG. 9c shows the affinity capture of IL-1α on the separation site SS, followed by elution, routing and subsequent incubation in the modifying site MS. Details of the procedure are given in the description of the illustration. Using the SPR data quantitatively, the IL-1α was digested for six-minutes using a 2:1 enzyme-to-substrate ratio (~190 fmole pepsin to 95 fmole IL-1α). FIG. 9d shows a mass spectrum taken directly from the pepsin-activated modifying site MS on the bioactive chip BC. Multiple signals ranging up to the parent molecular mass of IL-1α are observed as a result of the digest. FIG. 9d inset shows the alignment of fragments with IL-1α sequence cleaved C-terminally to F, L, E and D.

One of the things this example demonstrates is the successful coupling of a separation site SS to a modifying site MS. As there is a substantial dead volume in the flow channels preceding the separation site SS, and in the flow channel between the two action sites, SPR detection was essential in tracking the location of the elution buffer throughout the microfluidics and on the surface of the bioactive chip BC. Furthermore, any changes occurring in the fluidics during the incubation period can be easily observed. The choice of elution buffer is also important because, in the two action sites arrangement shown in this example, it must be compatible with both elution of the analyte from the separation site SS and enzyme activity on the modifying site MS. For this reason, pepsin was chosen as digest enzyme rather than more specific enzymes that are active at pH~7. The pH 2.5 citrate buffer is able to break the antibody/antigen interaction in the separation site SS, and is optimal for pepsin digestion in the modifying site MS. It is also important to note that the entire process, from initial injection of analyte to introduction into the mass spectrometer took ~30 minutes. Prolonging the capture/rinse/digest process ultimately results in less sample available for mass spectrometric analysis due to e.g., dissociation from the receptor (during extended rinsing, as observed by the SPR data) and loss of proteolytic fragments through absorption to the microfluidics or the bioactive chip BC upon complete drying of the digest mixture.

EXAMPLE 9

Figure 10A:
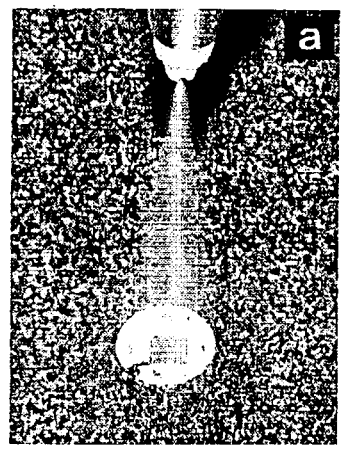
FIG. 10 illustrates the aerosol MALDI matrix application onto a bioactive chip BC. (a) A fine mist of matrix solution is created through the use of an aerosol applicator. (b) The appearance of the bioactive chip BC following drying of the matrix solution, showing spatial resolution between the action sites on the bioactive chip BC. (c) Enlarged view of the two action sites on the bioactive chip BC following matrix application.
Figure 10B:
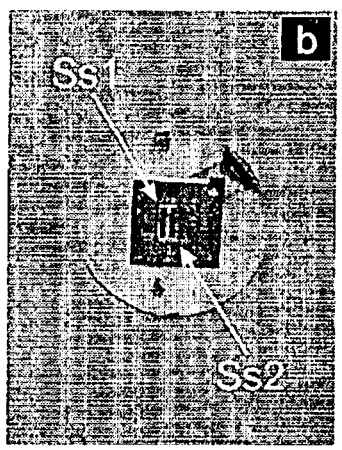
Figure 10C:
Figure 11:
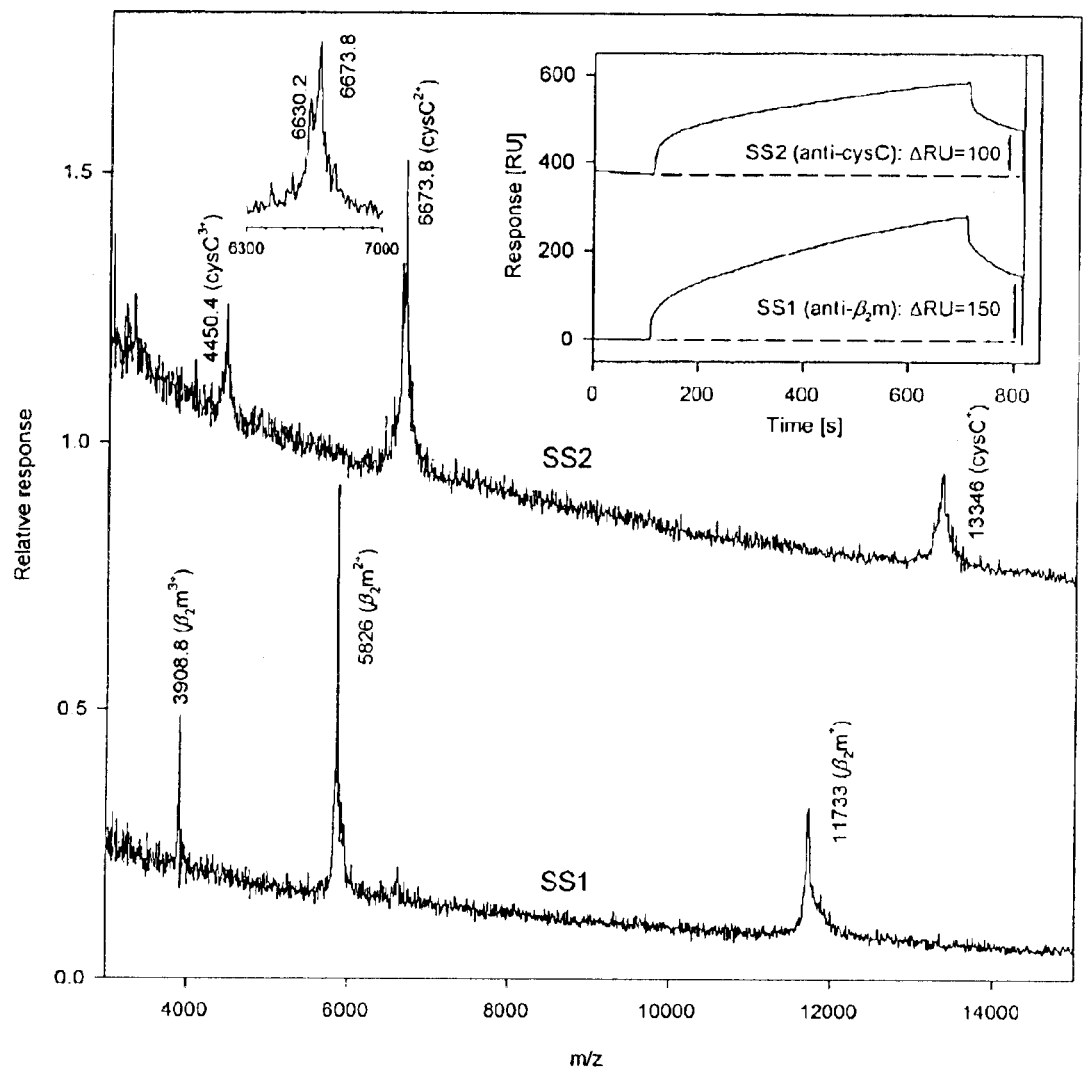
FIG. 11 illustrates the importance of the aerosol matrix delivery approach in accurately performing BCMS. An aliquot of diluted human plasma solution (50 fold dilution with running HBS buffer) was injected simultaneously over the surface of anti-$\beta$2m derivatized separation site SS1 and anti-cysC derivatized separation site SS2 (sensorgrams shown in the inset). Following MALDI matrix application via the aerosol delivery approach, MALDI-TOF mass spectrometry was performed from the surface of each separation site SS. The signals in the MALDI-TOF mass spectrum taken from the first separation site SS1 indicate the presence of $\beta_2$m only, ($MW_{\beta 2m}$=11729.2). The signals in the MALDI-TOF mass spectrum taken from the second separation site SS2 indicate the presence of cysC only ($MW_{cysC}$=13343.2). The signals in the mass spectra indicate that the spatial resolution between the two action sites was maintained during matrix application.

Use of Aerosol MALDI Matrix Application on a Bioactive Chip BC and Spatial Resolution of Action Sites In this example, an importance of proper matrix application on the bioactive chip BC is demonstrated in that the resolution between the action sites on the bioactive chip BC existing during the interaction analysis IA is further maintained in the subsequent mass spectrometry analysis performed from different action sites on the bioactive chip BC. Two separation sites SS (SS1 and SS2) on a bioactive chip BC were utilized: the surface of the first separation site SS1 was derivatized with anti beta-2-microglobulin (anti-$\beta_2$m) antibody; the surface of the second separation site SS2 was derivatized with anti-cystatin C (anti-cysC) antibody. Sensorgrams of a 50 μL injection of a diluted human plasma solution (50 fold dilution with running HBS buffer) simultaneously over the surface of both separation sites SS1 and SS2 are shown in FIG. 11 inset. Following a short buffer wash, the bioactive chip BC was removed from the SPR-biosensor and saturated aqueous solution of MALDI matrix (α-cyano-4-hydroxycinnamic acid, in 33% (v/v) acetonitrile, 0.2% (v/v) trifluoroacetic acid) was applied on the entire bioactive chip BC surface using the aerosol delivery approach depicted in FIG. 10. Using this approach, a thin, homogeneous matrix layer over the entire surface of the bioactive chip BC is produced. The homogeneity of the surface allows repetitive and reproducible spectra to be obtained over the entire area of an active site. Of equal importance, a "cross-talk" between the action sites is not allowed and spatial resolution between action sites on the bioactive chip BC is preserved. The signals in the MALDI-TOF mass spectra taken from the surface of each separation site SS (FIG. 11) indicate $\beta_2$m binding on the first separation site SS1 (MW$\beta_{2m}$=11729.2) and cysC on the second separation site SS2 (MW$_{cysC}$=13343.2), as expected from each separation site's specificity (the accompanying smaller mass signal in the cysC spectrum indicate a removal of the N-terminal cysC serine residue). The signals in the mass spectra indicate that the spatial resolution between the two separation sites was maintained during matrix application.

OTHER ANALYTICAL METHODS

In another aspect of this invention, methods other than SPR are employed to perform real-time, non-labeling analysis of the captured analyte. Such analysis may be obtained by various detection systems. In a suitable type of detection system, a change in a property of the sensing structure is measured as being indicative of binding interaction at the sensing surface. Among these methods are, for example, mass detecting methods, such as piezoelectric, optical, thermo-optical and surface acoustic (SAW) methods, and electrochemical methods, such as potentiometric, voltametric, conductometric, amperometric and capacitance methods. It is also possible to use short-range radioactivity, such as scintillation plastics in close proximity to the interaction position of $^3$H or other short-range ionizing radiation.

Suitable optical methods of analysis include those that detect surface refractive index and or thickness, such as reflection-optical methods, including both internal and external reflection methods, e.g. ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave based imaging, such as critical angle resolved imaging, Brewster angle resolved imaging, SPR angle resolved imaging, and the like, as well as methods based on evanescent fluorescence (TIRF) and phosphorescence. Additionally, optical methods based on interference may be used for surface binding detection. Further, optical methods here include surface-based chemiluminescence and electroluminescence. Still another surface-based optical method included here is surface enhanced Raman spectroscopy and surface enhanced resonance Raman spectroscopy.

The preferred embodiment(s) of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A method for analyzing one or more analytes comprising the steps of:
   providing a flat surface of a chip having at least one separation site and at least one processing site;
   performing at least one of separating and processing the one or more analytes by non-covalently attaching the one or more analytes to at least one of the separation and processing sites;
   spraying a MALDI matrix solution over the flat surface;
   rapidly drying a matrix/analyte mixture contained on said flat surface; and analyzing the one or more analytes by performing MALDI mass spectrometry from said flat surface.

2. The method of claim 1 wherein the step of spraying comprises spraying with an aerosol applicator having an aspirating/sheath gas needle backed by compressed air.

3. The method of claim 1 wherein the step of analyzing the one or more analytes comprises using the flat surface containing the matrix/analyte mixture as a target for performing the MALDI mass spectrometry.

4. The method of claim 3 wherein the step of presenting one or more analytes on a flat surface further comprises the step of presenting one or more analytes on a flat surface of a plasmon resonance-active chip.

5. The method of claim 1 wherein the step of presenting the one or more analytes on a flat surface comprises the step of presenting one or more proteins on a flat surface.

6. A method for analyzing one or more analytes comprising the steps of:
   providing a flat surface of a chip having at least one separation site and at least one modifying site;
   performing at least one of separating and modifying the one or more analytes by non-covalently attaching the one or more analytes to at least one of the separation and modifying sites;
   spraying a MALDI matrix solution over the flat surface;
   rapidly drying a matrix/analyte mixture contained on said flat surface; and analyzing the one or more analytes by performing MALDI mass spectrometry from said flat surface.

7. The method of claim 6 wherein the step of spraying comprises spraying with an aerosol applicator having an aspirating/sheath gas needle backed by compressed air.

8. The method of claim 6 wherein the step of analyzing the one or more analytes comprises using the flat surface containing the matrix/analyte mixture as a target for performing the MALDI mass spectrometry.

9. The method of claim 8 wherein the step of presenting one or more analytes on a flat surface further comprises the step of presenting one or more analytes on a flat surface of a plasmon resonance-active chip.

10. The method of claim 6 wherein the step of presenting the one or more analytes on a flat surface comprises the step of presenting one or more proteins on a flat surface.

* * * * *